(12) United States Patent
Stobbe

(10) Patent No.: US 9,677,038 B2
(45) Date of Patent: *Jun. 13, 2017

(54) DEVICE AND METHOD FOR INDUSTRIAL CULTIVATION OF CELLS

(75) Inventor: Per Stobbe, Holte (DK)

(73) Assignee: STROBBE PHARMA TECH GMBH, Chiasso (CH)

( * ) Notice: Subject to any disclaimer, the term of this patent is extended or adjusted under 35 U.S.C. 154(b) by 524 days.

This patent is subject to a terminal disclaimer.

(21) Appl. No.: 13/806,402

(22) PCT Filed: Jun. 21, 2011

(86) PCT No.: PCT/EP2011/060303
§ 371 (c)(1),
(2), (4) Date: Mar. 4, 2014

(87) PCT Pub. No.: WO2011/161086
PCT Pub. Date: Dec. 29, 2011

(65) Prior Publication Data
US 2014/0227769 A1    Aug. 14, 2014

(30) Foreign Application Priority Data

Jun. 23, 2010 (DK) .................................. 2010 00548
Jun. 23, 2010 (DK) .................................. 2010 00549

(51) Int. Cl.
*C12M 1/12* (2006.01)
*C12M 1/00* (2006.01)
(Continued)

(52) U.S. Cl.
CPC ............. *C12M 25/18* (2013.01); *B01D 27/14* (2013.01); *C12M 23/34* (2013.01); *C12M 23/42* (2013.01);
(Continued)

(58) Field of Classification Search
CPC ....... B01D 27/14; C12M 23/34; C12M 23/42; C12M 23/44; C12M 25/14; C12M 25/18;
(Continued)

(56) References Cited

U.S. PATENT DOCUMENTS

| 4,201,845 A | 5/1980 | Feder et al. |
| 4,546,083 A | 10/1985 | Meyers et al. |

(Continued)

FOREIGN PATENT DOCUMENTS

| EP | 0112155 A2 | 6/1984 |
| EP | 0155237 A2 | 9/1985 |
| WO | 2007039600 | 12/2007 |
| WO | 2007142664 | 12/2007 |

OTHER PUBLICATIONS

International Search Report, dated Feb. 14, 2012, for application No. PCT/EP2011/060303 filed Jun. 21 2011.
(Continued)

*Primary Examiner* — Michael Hobbs
(74) *Attorney, Agent, or Firm* — Cheryl H Agris; Agris & von Natzmer, LLP

(57) ABSTRACT

A compact, high-yield, bio-reactor for use as small, medium and large-scale production unit for hosting and culturing of stem cells or living cells or micro organism and producing by multiplication or expression one or more biologic compounds for medical and biological applications.

22 Claims, 11 Drawing Sheets

Figure 1:
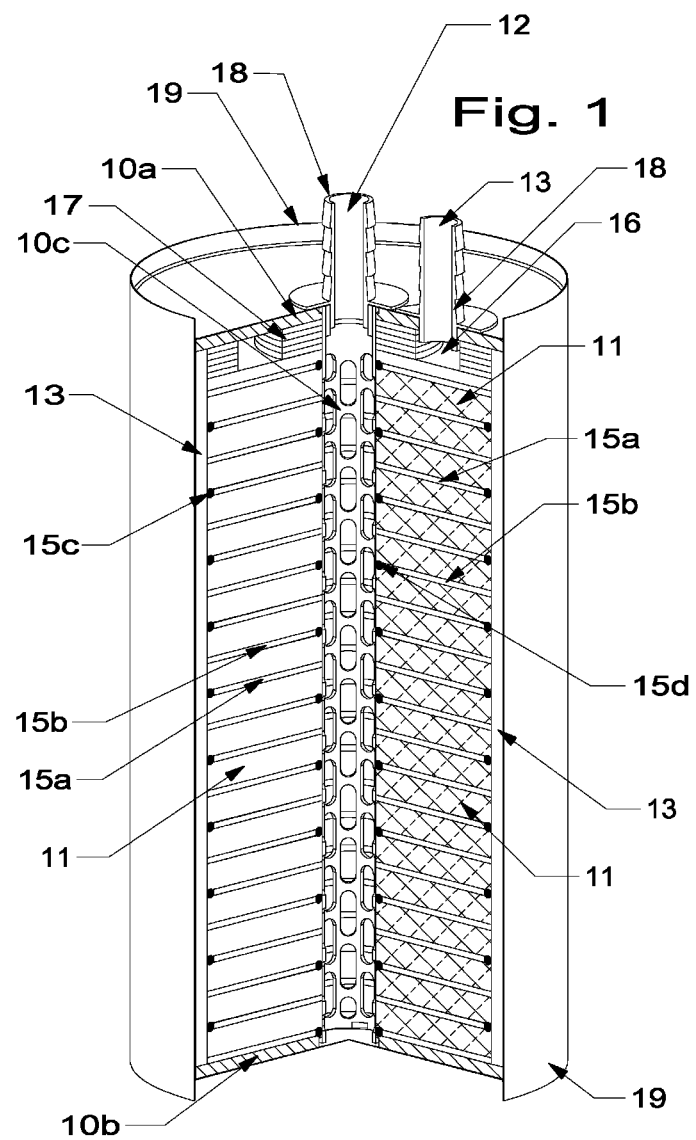

(51) Int. Cl.
 *C12M 3/00*  (2006.01)
 *B01D 27/14* (2006.01)
 *C12N 5/074* (2010.01)
 *C12N 9/00*  (2006.01)
 *C12P 19/04* (2006.01)
 *C12P 21/00* (2006.01)

(52) U.S. Cl.
 CPC ............ *C12M 23/44* (2013.01); *C12M 25/14* (2013.01); *C12M 29/04* (2013.01); *C12M 29/10* (2013.01); *C12M 47/10* (2013.01); *C12N 5/0607* (2013.01); *C12N 9/00* (2013.01); *C12P 19/04* (2013.01); *C12P 21/00* (2013.01)

(58) Field of Classification Search
 CPC ...... C12M 29/04; C12M 29/10; C12M 47/10; C12N 5/0607; C12N 9/00; C12P 19/04; C12P 21/00
 See application file for complete search history.

(56) References Cited

U.S. PATENT DOCUMENTS

| | | | |
|---|---|---|---|
| 5,266,476 A | 11/1993 | Sussman et al. | |
| 5,501,971 A | 3/1996 | Freedman et al. | |
| 5,543,047 A | 8/1996 | Stoyvell et al. | |
| 5,563,069 A | 10/1996 | Yang | |
| 6,844,187 B1 * | 1/2005 | Wechsler | C12M 29/04 |
| | | | 435/297.2 |
| 9,228,579 B2 * | 1/2016 | Stobbe | C12M 23/34 |
| 2008/0003676 A1 | 1/2008 | Sheridan et al. | |
| 2009/0029434 A1 * | 1/2009 | Tsai | C12M 21/12 |
| | | | 435/170 |

OTHER PUBLICATIONS

Written Opinion of International Searching Authority, dated Feb. 14, 2012, for application No. PCT/EP2011/060303 filed Jun. 21 2011.
International Preliminary Report on Patentability, dated Aug. 10, 2012 for related application No. PCT/EP2011/060303.

* cited by examiner

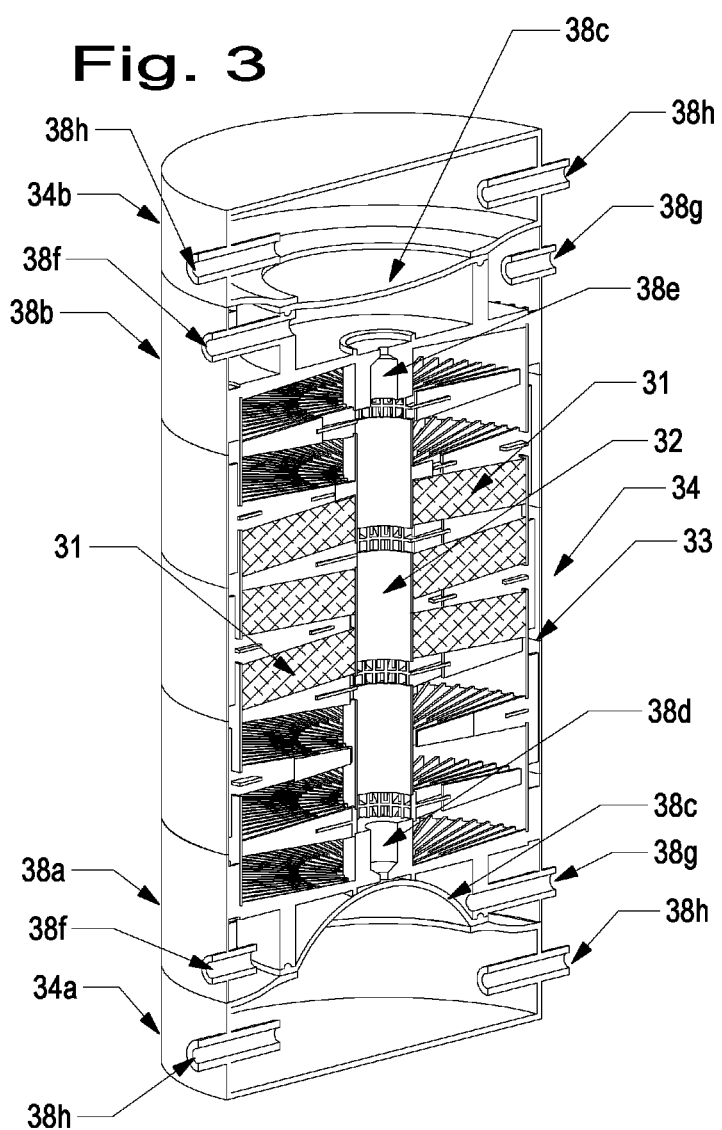

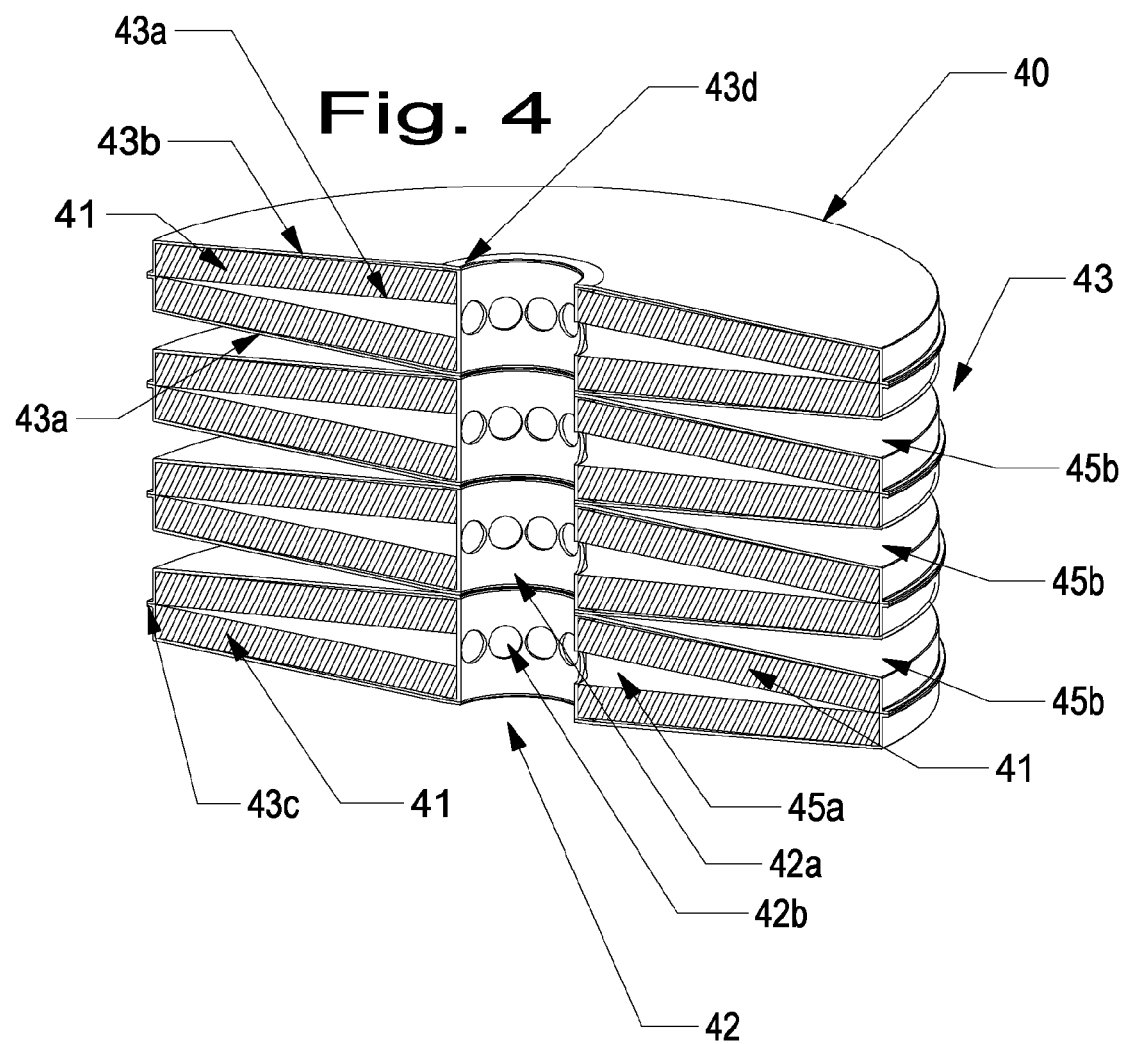

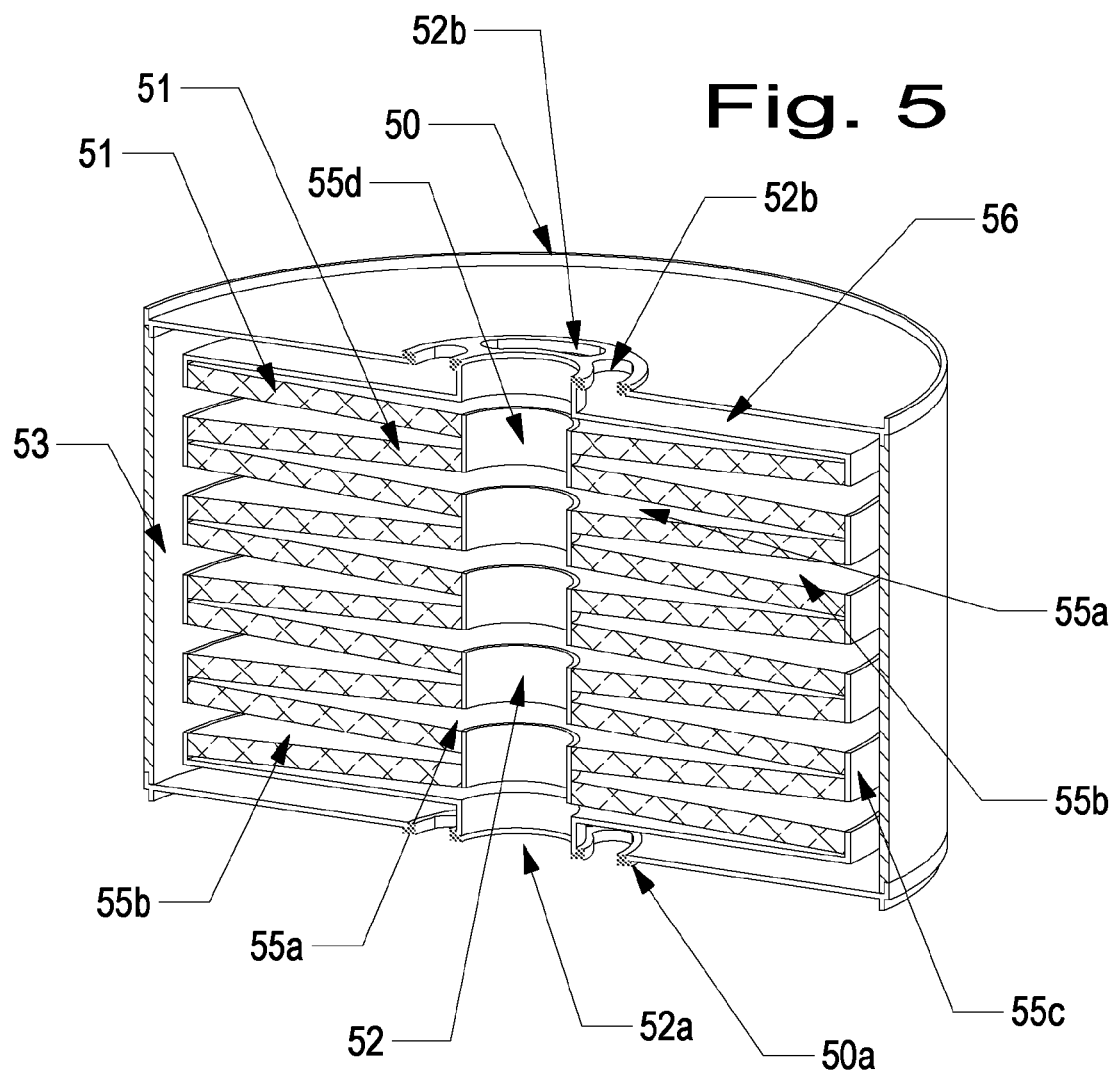

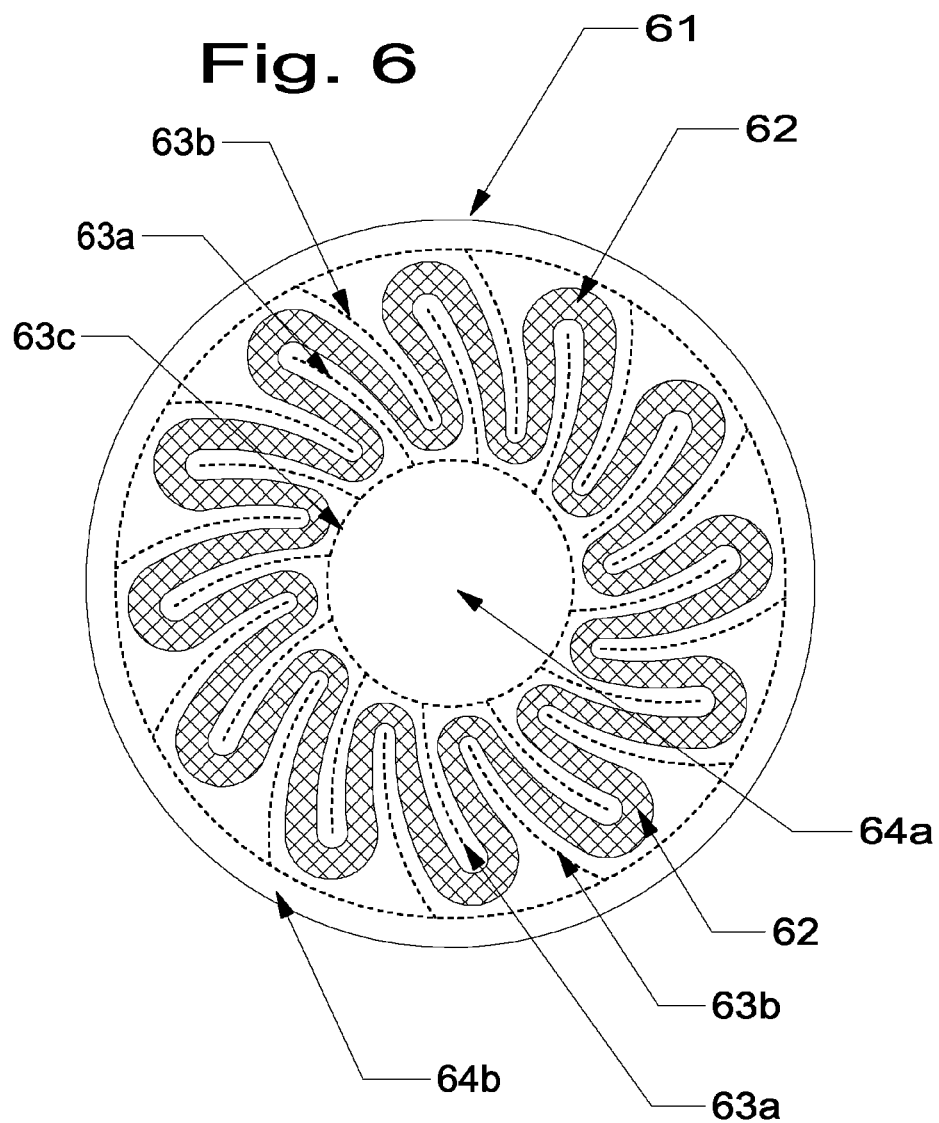

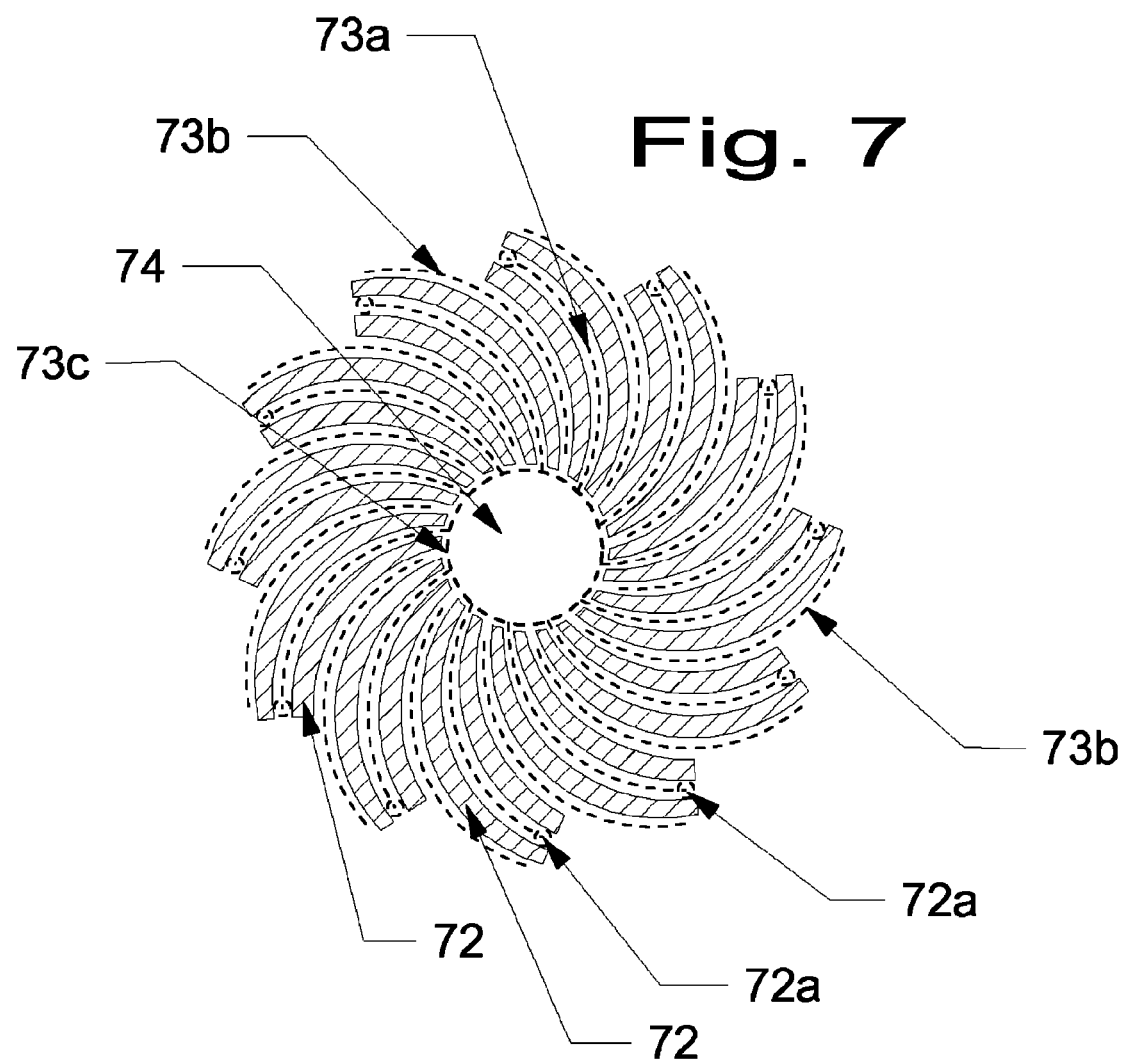

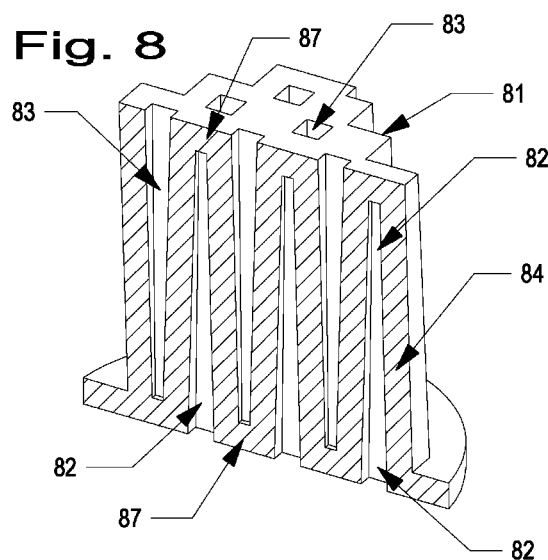
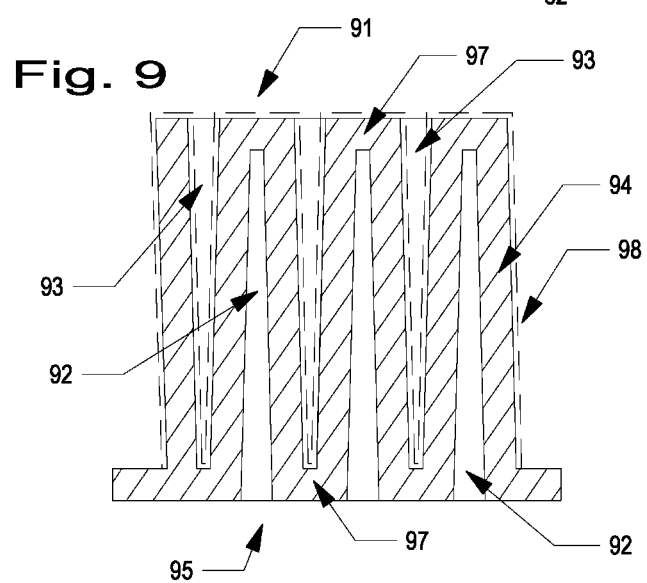

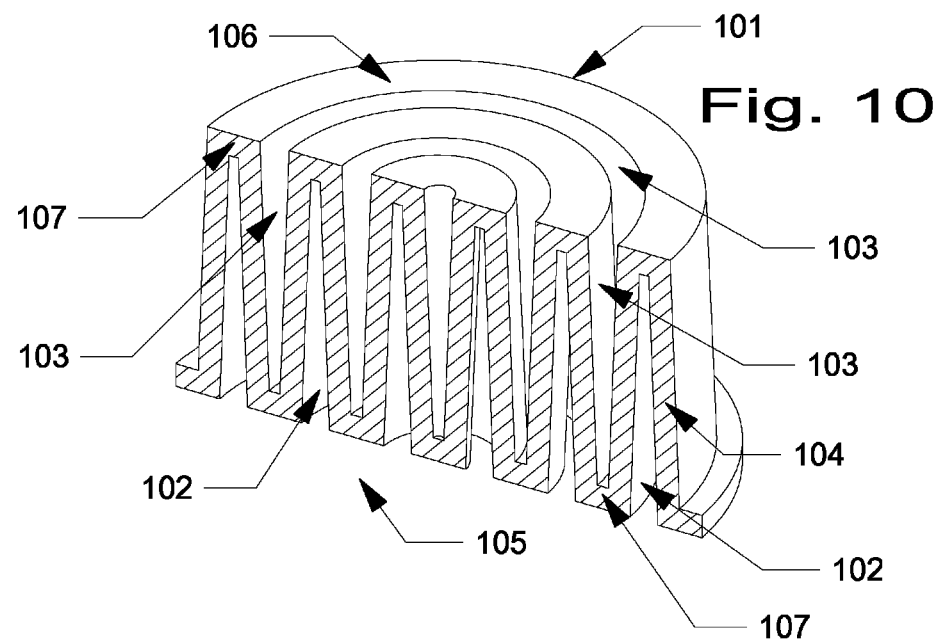
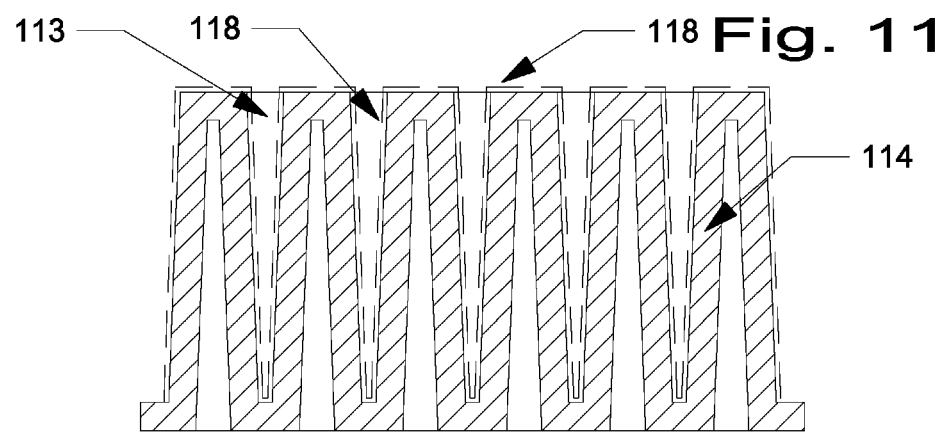

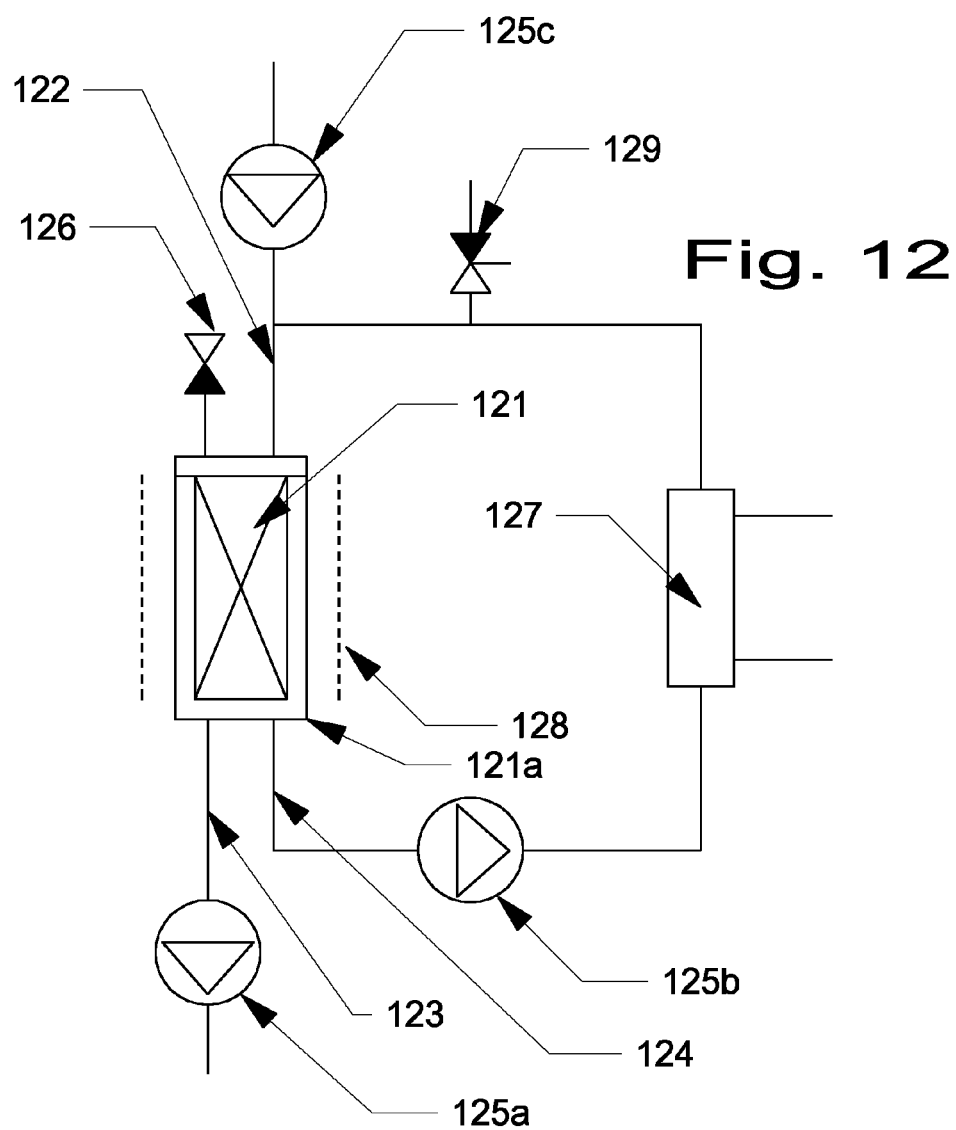

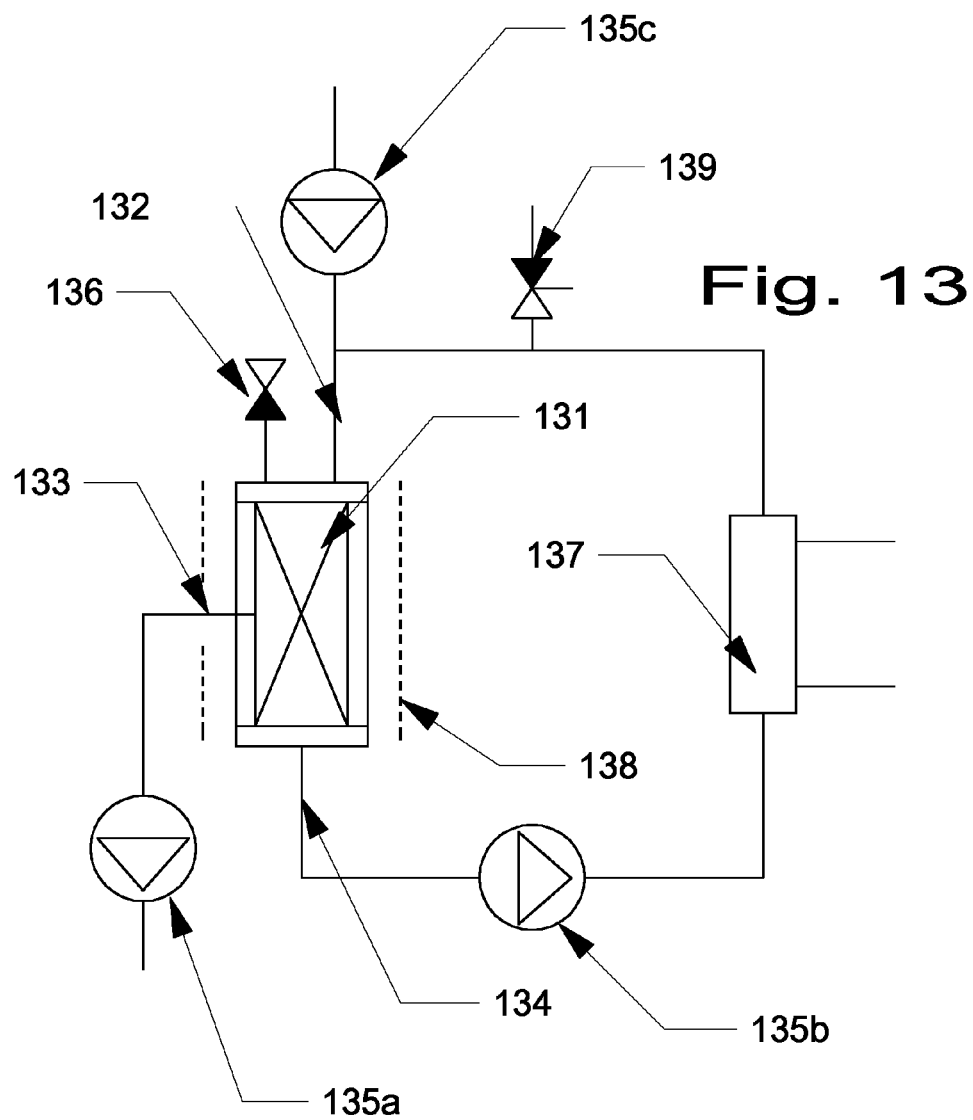

DEVICE AND METHOD FOR INDUSTRIAL CULTIVATION OF CELLS

TECHNICAL FIELD

The present invention relates to a device, such as a bio-reactor or a bio-reactor module, for expression or proliferation of a biologic material and a process creating a stem cell or living cell or biological cell or micro organism friendly environment for use in a bio-reactor and methods for operating said bio-reactor.

BACKGROUND OF THE INVENTION

Bio-reactor design and operation is a complex engineering task. Under optimum conditions, cultivated stem cells and living cells must be able to perform their desired production with a 100 percent rate of success. The bio-reactor's environmental conditions, like gas content (i.e., air, oxygen, nitrogen and carbon dioxide), flow rates, temperature, pH and agitation speed/circulation rate need to be closely monitored and controlled.

A bio-reactor is a suitable device for cultivating stem cells or living cells or micro organisms being adherent and semi-adherent dependent or in suspension. Ideally, any stem cell or living cell or micro organism cultivating bio-reactor must maintain sterile conditions. In the aerobic process, optimal oxygen transfer and access is perhaps the most difficult task to accomplish. Oxygen is poorly soluble in water at atmospheric pressure, even less in cultivation broths, usually helped by agitation, which is also needed to mix nutrients and to keep the production homogeneous. There are, however, limits to the speed of agitation in stirred tank bio-reactors, due both to high power consumption and damages to the cultivated stem cells or living cells or micro organisms.

In bio-reactors the goal is to cultivate stem cells or living cells or micro organisms for mass production of stem cells or living cells for medical application, as regenerative medicine and therapeutic applications or drugs or more traditional expression from living cells or micro organisms of molecules for therapeutic purposes or as drugs.

Prior Art

U.S. Pat. No. 5,501,971 (New Brunswick Scientific) describes the Celligen system in the form of a packed bed of FibreCell polyester fibre based, flat carriers. The system currently on the market from New Brunswick Scientific demonstrates that cells at least semi-adhere well to a polyester fibre, but the Celligen system is heavily limited by the thickness of the bed. As an increased bed thickness introduces or increases undesirable gradients in the bio-reactor, the bio-reactor device is not scalable and can be used for cultivations on a bench-top scale only.

U.S. Pat. No. 5,266,476 (Yeda) discloses a matrix of a thickness of from 50 to 500 µm and a surface area of 1 millimeter$^2$. The matrix is based on a polyester fibre and is in the form of a very small carrier know in the industry under the trade name FibraCell (supplied by both NBS and Bibby Sterilin Ltd, UK). FibraCell is a mini body approx. 6 millimeter in diameter and 0.6 millimeter thick. FibraCell has been used for various applications, among others by NBS (New Brunswick Scientific, USA) for manufacturing the Celligen product in which Fibra Cell bodies are randomly and efficiently packed in volumes of up to 1 liter. Larger reactor volumes are not possible due to gradient problems.

U.S. Pat. No. 4,546,083 (Stoll Corp) discloses a cylindrical device with fibres positioned around a tubular inlet—a spindle. The volume for the fibre matrix between the spindle and the cartridge inner wall are filled with loosely packed fibres only.

U.S. Pat. No. 5,543,047 (Pall, Inc) describes a special pleating method improving among others also the potential area/volume ration and as described for filtration purposes only.

U.S. Pat. No. 5,563,069 (Ohio State University) is concerned with a packed bed structure based on cotton cloth in sheet shape.

WO2007/142664 (AMProtein Corp) discloses a method for increasing dissolved oxygen in a culture medium for semi-adherent or suspension culture of mammalian cells in a vessel. The vessel concept exploits constant height and varies the diameter in order to vary the fermenter volume in order to handle the gradient issue.

WO2007/039600 (Artelis) discloses a complicated flow pattern vessel device, which has an integrated mixer operating as circulation pump. The device is not suitable for up-scaling due to an undesirable increase in nutrient and/or oxygen gradients. Media re-circulation is performed by a mixer device internally in the vessel and this feature also seriously limits the prospects for up-scaling. Only perfusion mode operation is described. Gradients occurring in the central inlet zone results in the generation of an un-even cell density in the modules. The invention is based on packed micro porous non-woven micro carriers present inside modules, envelopes for cell support and/or empty modules suitable for the suspension of cells. Each radial fluid inlet between two envelopes supply media to only one of two envelopes. As described, most of the cells are not circulated, but those which are will be subjected to strong shear forces generated by the mixer impeller. Such cells are at risk of being seriously damaged. The described mixer physics exploit very limited pressure difference capabilities, limiting the scale-up of the concept and further increases shear forces in the fluid significantly.

US2008/0003676 describes a method of growing embryonic stem cells in contact with a surface of a porous membrane covered with feeder cells. A porous matrix being an embodiment considerably thicker than the described membrane is not described nor is the use of polyester material or polyester fibres comprising the permeable body described.

The journal "BioProcess International" published in June of 2009 carries an article wherein AMprotein (China) states that they use large, randomly oriented, loosely packed cellulose fibre bodies, or Rasching alike soft elements, as "macro"-carriers for bio-reactor cultivations. It appears that the "Current" bio-reactor packed bed height is constant at approx. 150 millimeters and that the volume is modified by using 3 different diameters according to a reactor size ranging from 5 liters over 50 liters to 150 liters, thereby avoiding the problem of how to solve the problem of gradient formation.

None of the above-cited prior art references have solved the gradient problems associated with "packed bed" bio-reactor cultivations. Also, none of the above-cited prior art references have solved the problem of how to effectively scale a bio-reactor from a bench-top level to industrial production scale without the concomitant generation of undesirable gradients in said bio-reactor.

BRIEF DESCRIPTION OF THE INVENTION

The present invention solves the problem of how to effectively scale a bio-reactor from a research scale over lab-scale over bench-top production level to an industrial scale production without the generation of undesirable gradients in the industrial scale bio-reactor.

The present invention also solves the problem of how to increase biological cell densities while at the same time reducing the volume of the bio-reactor in which the micro organisms are semi adherent and/or in suspension. This increased "compactness" of the bio-reactors according to the present invention reduces the cost of manufacturing facilities needed for industrial scale bio-reactors.

The present invention is further designed to fulfil the current and future request from the pharmaceutical industry by being of single-use capability here reducing or completely eliminating the time consuming and very cost cleaning of current stainless steel process equipment and associated validation.

Accordingly, the present invention in a first aspect provides a gradient free, bio-reactor device and methods of efficiently cultivating stem cells and living cells for proliferation.

Accordingly, the present invention in a second aspect provides a gradient free, bio-reactor device and methods of efficiently cultivating live biological cells, such as e.g. living cells or micro organisms. According to the methods of the present invention, bio-molecules such as e.g. proteins, such as recombinant proteins, recombinant antibodies, monoclonal antibiotics, viral and recombinant vaccines and secondary metabolites can be more efficiently produced.

In one embodiment the micro organisms, such as stem cells are by nature adherent or semi-adherent to surfaces within permeable bodies or becomes adherent to other cells or by agglomeration semi-adherent between said surfaces of the scaffolding within permeable bodies. Said permeable bodies forming permeable stocks, such as essentially spherical envelopes or discs of a predetermined thickness, wherein said stocks or bodies or discs comprise a porous matrix. The porous matrix comprises a plurality of inter-connected, open pores and essentially no closed pores in the scaffolding. The selected size of the open pores of the matrix allows micro organism to be hosted and cultivated within said pores of the matrix material and habitat, colonize the internal volume of said porous matrix.

In one other aspect the biological cells are introduced during seeding to the bioreactor in suspension and continue being supported in a suspension within the matrix cavities and not specifically semi-adhere to the porous matrix surfaces, but kept in agglomerated stage within the matrix boundaries or combination of semi-adhering and suspension.

The above is important as some biological cells is considered to be adherent or semi-adherent to surfaces and other adherent by nature micro organisms is trained to be solely in suspension for which the present invention clearly handles both or any type or variation. By nature most micro organisms are adherent and by training converted to be non adherent. Over time micro organisms starting living in suspension will slowly convert to be adherent again.

Due to a high surface area/disc volume ratio, cultivation of a density of biological cells can be supported. Due to i) bio-reactor fluid handling design and ii) the physical nature of the matrix of the employed permeable bodies, discs or envelopes, the biological cells or micro organisms do not experience undesirable gradients in e.g. nutrients and oxygen and the vast majority of cells are supplied with sufficient nutrients and oxygen. Bio-reactors and methods of the present invention are designed so as to ensure an efficient culturing of biological cells, such as stem cells or living cells or micro organisms, by allowing a feeding liquid comprising nutrients to obtain an essentially gradient free contact with biological cells semi-adhered to bio-compatible surfaces and matrices of e.g. permeable bodies or discs.

The permeable bodies, disc or envelopes according to the present invention can be of any form and shape. In one embodiment the discs, bodies or envelopes are circular with an optionally cut-out central portion to allow for the adaptation of a feeding tube or harvesting tube or a collection reservoir in operable contact with the discs. The height (i.e. thickness) of the disc, body or envelope is preferably ranging 1 to 500 mm.

The diameter of the bodies, discs or envelopes will depend on the reactor design, including the height of the discs, bodies or envelopes and the diameter is, in one embodiment, preferably 1 to 1,000 centimeters, e.g. 1 to 500 centimeters.

The fibres of the permeable bodies, discs or envelopes preferably has, in one embodiment, an average diameter in the range of from 0.01 micrometer to preferably less than 500 micrometers The packing density of the permeable bodies, disc or envelopes is preferably, in one embodiment, in the range of from of from 10 to 5,000 gram/dm$^3$, e.g. from 100 to 5,000 gram/dm$^3$.

Preferably, the volume of the open pores of the matrix of the permeable bodies, disc or envelopes is preferably more than 20% and less than 99%, e.g. more than 20% and less than 98%.

The number of permeable discs/stacks/bodies/envelopes present in the bio-reactor, or a module thereof, can be any number, preferably a number of from 2 to 100, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100.

The bioreactor of the present invention may according to one embodiment comprise a porous matrix, one or more bio-reactor inlet port(s) and one or more bio-reactor outlet port(s), wherein biological cells, micro organisms are capable of partially adhere to surfaces or to adhered feeder cells on said surface on said permeable bodies within a suspension and/or capable of agglomeration within a suspension, residing in at least some and preferably all of the inter-connected, open pores or cavities of said permeable bodies, wherein said matrix separates said one or more bio-reactor inlet port(s) from said one or more bio-reactor outlet port(s), wherein said matrix comprises individual matrix sections each separated by a spacer section for diverting feeding liquid to or from said individual matrix sections.

Each of such "individual matrix section" can comprise a plurality, as for example at least 2, "individual matrix sub-sections", wherein each such sub-section is separated from another sub-section by a permeable layer comprising a plurality of openings exerting a biological cell retaining function, but not a feeding liquid retaining function, wherein the diameter of the openings of the permeable layer is smaller than the diameter of the biological cells to be cultivated, thereby creating a layer in between individual matrix sub-sections which is capable of diverting feeding liquid in a direction essentially perpendicular to the direction in which feeding spacers and drainage spacers are diverting feeding liquid to and from, respectively, the individual matrix sections.

The thickness of an individual "permeable layer", or the collective thickness of a plurality of "permeable layers" dividing an individual matrix section into a plurality of sub-sections, is preferably less than 90% of the thickness of the individual matrix section comprising said one or more permeable layer(s). The one or more permeable layer(s) preferably divide an individual matrix section into sub-sections having at least essentially similar thickness, i.e. no sub-section differs in thickness by more than 50% from any other individual matrix sub-section.

The permeable layer(s), when present, ensures that feeding liquid can flow from a feeding liquid spacer either through the individual matrix sections, or through the permeable layer, thereby further reducing and/or eliminating gradients of feeding liquid nutrients in the bio-reactor. Without being bound by theory, it is believed that the flow rate of feeding liquid along the permeable layer will be faster than the flow rate of feeding liquid through the individual matrix parts. However, it is also possible that under some practical conditions of bio-reactor operation, the flow along flow rate of feeding liquid along the permeable layer will be slower than the flow rate of feeding liquid through the individual matrix parts. Under such practical circumstances the feeding liquid being diverted along the permeable layer can be regarded as a supplemental source of feeding liquid useful for obtaining and sustaining optimal biological growth conditions.

In one aspect of the present invention there is provided a bio-reactor comprising a plurality of permeable discs/stacks/bodies/envelopes comprising a matrix comprising a plurality of fibres or growth bodies defining a plurality of inter-connected, open pores extending through at least part and preferably all of each discs/stacks/bodies/envelopes,
  wherein biological cells, micro organisms are capable of partially adhere to surfaces or adhered feeder cells on said surface on said permeable bodies within a suspension and/or capable of agglomeration within a suspension, residing in at least some and preferably all of the inter-connected, open pores of said permeable bodies,
  wherein the plurality of permeable discs/stacks/bodies/envelopes are alternately separated by feeding spacer sections and drainage spacer sections, respectively, so that each feeding spacer section provides feeding liquid to each of a first set of two adjacently located, permeable discs/stacks/bodies/envelopes and so that each drainage spacer section receives feeding fluid from each of a second set of two, adjacently located, permeable discs/stacks/bodies/envelopes,
  wherein each discs/stacks/bodies/envelopes is contacted by one feeding spacer section and one drainage spacer section, respectively, on opposite sides of the discs/stacks/bodies/envelopes,
  wherein essentially all feeding liquid entering the disc from the side of the discs/stacks/bodies/envelopes on which the feeding spacer section is located is diverted through the discs/stacks/bodies/envelopes and exits the discs/stacks/bodies/envelopes on the opposite side of the discs/stacks/bodies/envelopes, where the drainage spacer section is located.

The first set of two adjacently located, permeable discs/stacks/bodies/envelopes and the second set of two adjacently located, permeable discs/stacks/bodies/envelopes have one discs/stacks/bodies/envelopes in common when the feeding spacer section and the drainage spacer section are positioned next to each other in the bio-reactor, i.e. when they contact opposite surfaces of one and the same discs/stacks/bodies/envelopes.

The overall flow of a feeding liquid through each disc is essentially in a direction which is perpendicular to the direction of the flow of feeding liquid along the feeding spacer section feeding said disc, i.e. the matrix material of the disc exerts a "cross-flow" effect on the feeding liquid. Likewise, once feeding liquid exits a disc it is diverted along the drainage spacer section in a direction which is also essentially perpendicular to the direction of flow of feeding liquid through the disc.

The open pores of the matrix of the permeable discs or envelopes are larger in diameter than the biological cells to be cultivated, thereby allowing said cells to reside in said open pores during all or part of the duration of the cultivation.

The bio-reactor may be fitted with, operate in connection with a suitable pump in order to ensure a desirable media flow rate or flux or pressure capability is obtained. The bio-reactor can also be fitted with sensors, such as single-use sensors and a control unit for controlling the seeding of micro organisms and the progression of the subsequent cultivation or proliferation.

In another aspect of the present invention there is provided a bio-reactor comprising a plurality of permeable discs or envelopes comprising a matrix comprising a plurality of fibres or growth bodies defining a plurality of inter-connected, predominantly open pores or cavities extending through at least part and preferably all of each envelopes,
  wherein biological cells, micro organisms are capable of partially adhere to surfaces or to adhered feeder cells on said surface on said permeable bodies within a suspension and/or capable of agglomeration within a suspension, residing in at least some of and preferably all of the inter-connected, open pores of said permeable bodies,
  wherein the plurality of permeable discs are alternately separated by feeding spacer sections and drainage spacer sections, respectively, so that each feeding spacer section provides feeding liquid to each of two adjacently located, permeable discs and so that each drainage spacer section receives feeding fluid from each of two, adjacently located, permeable discs,
  i) a plurality of permeable discs comprising a matrix comprising a plurality of fibres defining a plurality of inter-connected, open pores extending through at least part and preferably all of the disc,
    wherein biological cells, micro organisms are capable of partially adhere to surfaces or adhered feeder cells on said surface on said permeable bodies within a suspension and/or capable of agglomeration within a suspension, residing in at least some and preferably all of the inter-connected, open pores of said permeable bodies,
    wherein the plurality of permeable discs are alternately separated by feeding spacer sections and drainage spacer sections, respectively, so that each feeding spacer section provides feeding liquid to each of two adjacently located, permeable discs and so that each drainage spacer section receives feeding fluid from each of two, adjacently located, permeable discs,
  ii) one or more inlet ports for diverting a feeding liquid to one or more feeding tubes of the reactor, iii) one or more axially elongated feeding tubes comprising a plurality of openings through which feeding liquid can be diverted to each of the plurality of permeable discs,
iv) a plurality of elongated and optionally cross-linked feeding spacers in liquid connection at a proximal end thereof with the one or more feeding tubes and extending in an essentially radial direction therefrom,
wherein feeding liquid can be diverted from said one or more feeding tubes to said plurality of feeding spacers through said holes of said one or more feeding tubes,
wherein the distal end of each feeding spacer is not connected to an outlet port for diverting feeding liquid to a collection reservoir,
wherein each feeding spacer separates two adjacently positioned permeable discs,
v) a plurality of elongated and optionally cross-linked drainage spacers in liquid connection at a distal end thereof with one or more outlet ports for diverting feeding liquid to a collection reservoir,
wherein the plurality of drainage spacers are located essentially in parallel to the plurality of feeding spacers,
wherein feeding liquid can be diverted from each of said plurality of feeding spacers and through a pair of neighbouring, permeable discs separated by a feeding spacer to one or more drainage spacers,
wherein the distal end of each drainage spacer is not connected to a feeding tube hole,
wherein each but end-positioned drainage spacer(s) separates two adjacently positioned permeable discs,
vi) a wall section comprising a plurality of collection reservoir outlet ports,
wherein each collection reservoir outlet port is in liquid contact with a collection reservoir, and
vii) a collection reservoir for collecting feeding liquid diverted to said collection reservoir from the permeable discs via drainage spacers and through said collection reservoir outlet ports.

The bio-reactor design variations when the permeable discs, envelopes are based on or include organic materials are e.g. such as:
1. Soft matrix bodies, scaffolding bodies based on fibres
2. Semi matrix rigid bodies based on fibres, particulates, grains, spheres
3. Porous matrix envelopes both based on and encapsulating growth bodies, such as compacted fibre, particulate, grain, sphere, carriers The bio-reactor design variations when the permeable discs are based on in-organic materials are e.g. such as:
1. Rigid matrix bodies based on particles, grains, spheres
2. Semi rigid matrix bodies based on fibre and particles, grain, spheres
3. Porous matrix envelopes both based on and encapsulating compacted fibre, particulate, grain, sphere, carriers The bio-reactor according to the present invention can in one embodiment be in the form of a single-use design with disposable capability for all or most of the components used.

The bio-reactor according to the present invention is in one embodiment fully scalable from lab-scale (0.0001-0.1 L) to bench-top level (0.1-15 L) to at least "small scale production size" (100-2,000 L).

The bio-reactor according to the present invention achieves in one embodiment an equipment volume reduction of at least 10, even 20 or 50 or 100 times compared to current suspension reactor bio material production capability.

The bio-reactor according to the present invention has in one embodiment a compact design for small foot print demand limited clean room facilities.

The bio-reactor according to the present invention is in one embodiment operated under conditions allowing an overall gradient free operation.

The bio-reactor according to the present invention achieves in one embodiment a cultivation based on a high cell density, such as more than $1\text{-}5 \times 10^8$ cells/mL.

The bio-reactor according to the present invention achieves in one embodiment a production capability of more than 0.1 or 0.5 or 1 or 2 gram/liter/day for laboratory scale production and more than 1 or 2 or 5 or 10 gram/liter/day for a pilot scale production.

The bio-reactor according to the present invention can in one embodiment employ integrated single-use sensors, thereby promoting the bio-reactor as a "single-use" bio-reactor. Depending on the selected materials, the bio-reactor of the present invention can either be autoclaved, otherwise sterilized or, when for "single use", be disposed of.

Accordingly, in one aspect the present invention is directed to an environmentally friendly, single-use, disposable bio-reactor. State-of-the-art single-use bio-container based bioreactors suffer from a number of draw-backs: Little proof of efficiency, no consideration of scaling, few systematic studies proving acceptable levels of leachables and extractables, absence of sensors, and finally no studies on the economics of converting multiple use systems to single-use systems.

As the market for single-use bio-reactors have matured over time and begun to address most of these issues, their market acceptance has rapidly expanded and a need exists for improved single use bio-reactors. When being designed for a single use application, the bio-reactor according to the present invention aims to achieve a number of objectives and the development of the single-use bio-reactor according to the present invention is driven by a reduction or elimination of sterilisation and cleaning requirements, an improved plant flexibility, elimination of a costly CIP cleaning-in-place operation and the associated validation of the CIP process, as well as reduced costs and faster time to market for the end product.

All of the above-cited benefits have been documented for the bio-reactor according to the present invention. Additionally, the bio-reactor according to the present invention clears many of the hurdles required by CMO's (Contract Manufacturing Organisation). These hurdles include the ability to add reliable, accurate, low cost sensors, so that standards can be generated and the process repeatability readily documented. It is unlikely that these hurdles will be fully cleared by simply re-applying the traditional methodologies of stainless steel and glass vessels to single-use bio-reactors. The distinct differences in construction materials and methods of use dictate that new solutions should be sought, which augment the advantages of single-use systems such as the bio-reactor disclosed herein when designed for a "single-use" operation. When being designed for a "single use" operation the bio-reactor preferably comprise materials which a re-cyclable, i.e. polymer based materials, rather than stainless steel and glass.

In one embodiment of the present invention the bio-reactor comprises stacked fibre based porous matrix sheets in the form of discs having a thickness ranging between 0.1 to 200 millimeter. The fibres have attractive surface properties for semi-adhering and general attraction of biological cells thereto and within the matrix pores, and the matrix pore size can be at least twice the size of the micro organisms to be cultivated (i.e. a pore size of from about 5 to 500 µm). The matrix discs or sheets stacked in sets and are alternately separated by nutrient feed spacers and drainage flow spacers. Multiple sets of matrix sheets or discs can be "squeezed" into a flow friendly and compact design. The design can have at least one central nutrient feed tube and a circumferential drainage reservoir, or vice versa. All nutrients preferably pass equally through each $cm^2$ matrix wall section, thereby eliminating nutrient and gas gradients. The reactor core of the bio-reactor is preferably enclosed in a close coupled film bag or container with integrated single-use sensors. The permeable bodies are preferably disposable, the sensors are also preferably disposable and the film bag or container can also be disposable so that the bio-reactor can be designed for 100% single-use.

Linear scaling up from laboratory scale to "small scale production" bio-reactors allows up-scaling from one non-woven disc OD (Outside Diameter) 47×L (Length) 4 millimeter/6 $cm^3$ to a multi disc set-up OD575×L1,000 millimeter in high=150,000 $cm^3$ creating the impressive scaling number of 1:25,000. With bio-reactor volumetric reduction of 1:40 the invented bio-reactor is equivalent (in biologic production capacity) to a suspension tank of 150,000×40=6 $m^3$.

Further the smallest bio-reactor body sized at 0.1 $cm^3$ and the largest being sized at OD1,000×L2,000 millimeter being app 1.5 $m^3$ creating the scaling number of 1:15,000,000.

In further embodiments nutrients and dissolved oxygen in the medium is preferably transported with no gradients through all the pores of the porous matrix of the employed discs to the micro organisms disposed partially on the surface and within the pores of the matrix. Each of the inlet feed channels (feeding spacers) in liquid contact with the feeding tube has no outlet port and thus cannot divert feeding liquid to a collection reservoir. The feeding spacers facilitate a forced flow of feeding liquid along the feeding spacer section in a direction away from the feeding tube(s), through the porous, permeable discs and further along an outlet channel (drainage spacer section) before entering a collection reservoir. The permeable discs of the bio-reactor have numerous porosity-determining, through-going pores permitting a free exchange of fluids and liquids from the carrier feed channels (feeding spacers) to drainage channels (drainage spacers). For bio-reactor applications the open pores within the porous matrix are preferably at least once the size of the hosted biological cells, including microorganisms. For separation applications, the opposite design with pores significant smaller than the micro organism applies.

The invented design solutions may find use within technical areas both within and outside the pharmaceutical industry, such as within the filtration, clarifying, retention and separation, cleaning, up-concentration, sterilization, ion-exchange. The presented design is further functional as a dept filter comprising an asymmetrical pore structure and/or an asymmetrically arranged fibre thickness and/or pore size within said matrix or membrane creating a gradient density matrix.

Definitions Relevant for the Present Invention

The term "anchorage dependent" or "adherent" as used herein refer to micro organism with affinity to anchor, adhered onto a surface, such as immobilised cells or stem cells or micro organisms in general adhering to growth bodies The term "bag" as used herein refers to a flexible (most often single-use) container made from plastic foil serving various purposes, media preparation and storage, bioreactor vessel, product storage The term "batch" as used herein refers to a bioreactor operation method to which no fresh media is added and no used media and/or cultured liquid removed The term "biological cells" as used herein is equivalent with micro organisms The term "biologics" and "biologics product" and "biologic material" as used herein are used interchangeable and refers to and includes a wide range of medicinal and therapeutic products and drugs such as: antibiotic, antibodies, recombinant antibodies, monoclonal antibodies, vaccines, proteins, recombinant proteins, proteins molecules, blood components, allergenics, somatic (adult) stem cells, tissues created by biological processes The term "bio mass" as used herein means renewable energy sources, biological products derived from living, or recently living organisms, such as wood, waste, (hydrogen) gas, and alcohol fuels The term "bioreactor" as used herein means a physical device, a container, a bag, a vessel which support biologically active environment suitable for cultivation of micro organism performing a process with the micro organism suspended in the media or containing inside a matrix or permeable body The term "capsule" as used herein refers to a series of containers integrating processing device(s) which may be circular and cylindrical or non circular or cylindrical, such as box shaped The term "cell density" describes the cell mass or amount of cells in a bioreactor The term "chemical compound" as used herein refers to a pure chemical substance consisting of two or more different chemical elements, such as organic molecules The term "chromatography" as used herein refers to a method for purification or capture involving a device that holds chromatographic active materials, typically one or more steps is needed in a purification process for protein capture and/or separations.

The term "cross flow mode operation" as used herein refers to operation principle for a filter unit The term "column" as used herein refers to a container, e.g. cylindrical container, assembled from two or more capsules stacked on top of each other into a column, a stack The term "cultivation" and "culturing" as used herein are used interchangeable and refers to hosting of micro organism in a bioreactor for production purposes, such as expression or proliferation The term "disposable" as used herein refers to a product manufactured from typically organic materials preferably taken from the group of polymers, thermo polymers, thermo setting polymers, and elastic polymers The term "expression" as used herein refers to production of molecules by micro organism being cultivated, but not to production of micro organism by multiplication or proliferation or by fermentation The term "envelope" as used herein defines a space or volume surrounded by a membrane or a wall of which some parts of the wall(s) are porous said envelope containing growth bodies and/or a matrix The term "fed-batch" as used herein refers to a bioreactor to which fresh medium is added and no cultured liquid removed until end of the process.

The term "feeder cells" as used herein refers to a coating on a surface with a adherent type of cell that synthesizes the extracellular matrix and collagen or fibroblast on top of which other cells, such as micro organisms or stem cells may semi-adhere to or agglomerate to The term "fermentation" as used herein refers to large scale hosting of micro organisms or single-celled living creatures for industrial purposes in a metabolic process creating a product which is not expression or proliferation The term "film" as used herein refers to thermoplastic film or foil made using an extrusion process typically in one or several layers of different material for different purposes. Films may be permeable or impermeable and translucent or coloured in thickness less than 1 mm.

The term "fluid" as used herein means liquids as well as gases

The term "filter" as used herein means a processing device which by size exclusion separates particles suspended in a fluid in a method named filtration or separation The term "filtrate" as used herein refers to the part of a suspension that passes through a filtration process, also called permeate The term "filtration" as used herein refers to mechanical separation, size exclusion, fractionating of solids from fluids, such as liquids or gases, by passing the feed stream through a porous material such as a porous, fibrous or granular substance, which retains selected solids and allows other solids and desired fractions of the fluids to pass through. Membrane filter products such as micro-filtration, ultra-filtration, nano-filtration, dia-filtration, gel-filtration are well known involving operation methods such as dead-end filtration, cross-flow filtration, The term "growth body or growth bodies" as used herein refers to micro beads, macro carriers, micro carriers, loosely packed fibres, fibres in general, non-woven, grains, spheres, Rasching bodies or fibrous bodies or rigid or semi rigid foam blocks either packed inside said envelope, or suspended inside said envelope The term "ion-exchange" as used herein refers to the exchange of ions between molecules, a solutions and a complex in the form of an insoluble sorbent, resin with typical physical appearance as beads or a membrane. The trapping of anions/cations takes place only with simultaneous releasing of other anions/cations; thus the process is called ion-exchange.

The term "impurities" as used herein refers to any substance that is not part of the biologic product, such as virus, HCP, DNA, RNA, Endotoxin The term "macro pore size" as used herein are ranging between 10-500 µm in diameter The term "matrix" as used herein defines a permeable body, porous body, such as a scaffolding structure such as a non-woven material or constituting growth bodies The terms "media", "growth media", and "nutrient" as used herein are used interchangeable and refers to a sterile complex mixture containing mostly water, carbon sources, various gases such as oxygen and additives such as; vitamins, hormones, growth factors, plant hydrolysates, animal serum, antibiotics, antioxidants, antifoams, cell stabilizers and other components for cultivation of micro organisms. Some media are serum based, some are serum free, animal free, and protein free or chemically defined media The term "meso pore size" are ranging between 1-10 µm in diameter The term "micro pore size" are ranging below 1 µm in diameter The term "membrane" between refers to a boundary layer, which serves as a selective barrier and remains impermeable to specific particles, molecules, substances or growth bodies or micro organisms when exposed to the action of a driving force (like a pump). Also a surface layer shaped as membrane(s) (typically attached to a more rigid carrier) with selected surface area, pore size, porosity, charge in order to increase contact and hereby affinity, adsorption, absorption of selected molecules, particles or the like.

The term "micro carriers" as used herein is a micro organism and stem cell supporting device allowing cultivation of adherent depending micro organisms and stem cells in suspension. Size range typical from 200 to more than 6,000 µm composed by gelatine, collagen, cellulose or glass and may further be functionalised with coatings. The micro carriers are in suspension inside said envelopes.

The terms "micro organism" or "microbial cell" or "cells" or "biological cells" as used herein are used interchangeable and is typically divided into: 1. living single-celled organisms, microbes such as; fungus, algae, moss, plankton, yeast, protozoa, eukaryotes, archaea, micro animals, extremophiles and plant cells or the like—2. adherent or semi adherent or suspended living cells such as animal cells, insect cells, mammalian cells, human cells, stem cells—3. prokaryotes and a variety of bacteria such as *E. coli* or the like—most of the above generically modified to solve specific tasks and product needs.

The term "non-woven" as used herein refers to a porous sheet, felt or web made from fibres, spun-bonded fibres or melt-blown fibres with small diameter ranging 5-100 µm in diameter, bonded together by, thermal and/or chemical and/or mechanical methods, which are neither woven nor knitted The term "oxygenator" as used herein refers to a sparging unit, bubble unit, a device or method for oxygen and/or carbon dioxide exchange from media to external sources The term "perfusion mode operation" as used herein refers to the operation method or principle for a bioreactor, the media are continuously exchanged, fresh nutrients added, used media removed and the crude product is harvested throughout the culture period The term "permeable body" as used herein defines an envelope, a matrix, a scaffolding, a volume including and/or being a porous body and/or a packed bed of growth bodies The term "polishing" as used herein refers to the final purification step(s) involving an affinity or other refined chromatography methods The term "pores" as used herein describe cavities or open spaces in a porous material expressed in micron size, such as 50 µm pore size.

The term "porosity" as used herein refers to a measure of the void spaces in a porous material expressed in percent 0-100%

The term "pre-filtration" as used herein refers to the early separation of waste (e.g. used and dead micro organisms, damaged micro organisms) from the crude product The term "proliferation" as used herein refers to a fast increase in numbers of a similar substance, a fast unlimited doubling, division of identical micro organism, multiplication of the micro organism or substance The term "protein" as used herein refers to complex organic macromolecules often primary ingredient in therapeutic medicine further proteins are present in each living cell of all organisms without exceptions and in the cells, the proteins are abundant in variety or types.

The term "purification" as used herein means a central part of the Down-Stream processing that takes a crude supernatant or cell homogenate (chaotic slurry of tissue and cells) and up-concentrates, isolates the biologic product in a fairly pure form. Involves processes such as filtration and chromatography in several difference forms The term "separation" as used herein means dividing fluid borne particles of different size by membrane filtration or centrifugal separation based on particle size, mass difference into at least two separate particle containing fluid streams further separation by affinity adsorbing the target compound The term "single-use" as used herein refers to a product designed for use only once and to be disposed after use typically delivered pre-sterilized and ready to use The term "suspension" as used herein refers to particles, micro organism depending on being suspended or mobilised in a fluid The term "suspension dependent" as used herein refers to micro organism, stem cells, cell lines suspended in a fluid with no or weak affinity to adhere to surfaces, such as micro organism of semi-adherent or of non-adherent character, though willing to agglomerate, willing to semi-adherent to similar micro organism, willing to semi-adherent to other micro organism by agglomeration or by other forces The term "stem cell(s)" as used herein refers to cells found in all multi cellular organisms. They are characterized by the ability to renew themselves through mitotic cell division and differentiate into a diverse range of specialized cell types. Stem cells of current international interest originate from humans and non human primates such as rat, rabbit, bovine, goat, sheep or marine creatures. Further stem cells in general, embryonic stem cells, pluripotent stem cells, induced pluripotent stem cells, adult (somatic) stem cells in general, regenerative stem cells, tissue-derived stems cells, stromal vascular fraction stem cells or the like The term "stacked" as used herein means two or more capsules positioned close, packed closely next to the neighbouring capsule other or on top of the neighbouring capsule

BRIEF DESCRIPTION TO THE DRAWINGS

Figure 2:
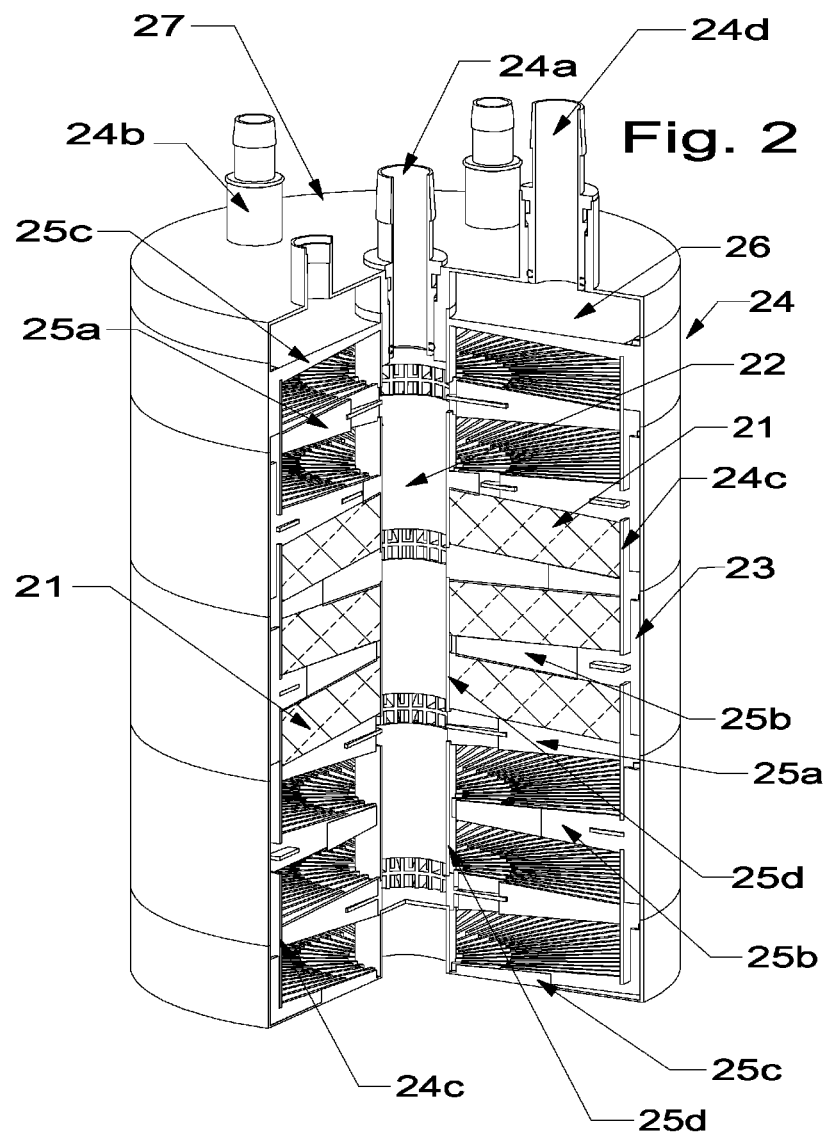

FIG. 1—The bioreactor in its most simple form in a flexible plastic bag
FIG. 2—The bioreactor housed in a rigid plastic cylinder
FIG. 3—The bioreactor integrated between two diaphragm pump modules
FIG. 4—A bioreactor based on envelopes covering a backed bed
FIG. 5—A bioreactor integrated with a capsule
FIG. 6—A pleated bioreactor
FIG. 7—A spiral bioreactor
FIG. 8—A square channel bioreactor seen in perspective
FIG. 9—A square channel bioreactor seen in cross section
FIG. 10—A circular channel bioreactor seen in perspective
FIG. 11—A circular channel bioreactor seen in cross section
FIG. 12—A method of operation
FIG. 13—A method of operation

DETAILED DESCRIPTION OF THE INVENTION

One embodiment of the present invention (version 1=matrix sections shaped like discs) features multiply stacked and in parallel operating permeable matrix sections preferably having a semi-deep bed configuration and an attractive internal surface area and/or volume based on compacted fibres assembled into a matrix inside an envelope (FIG. 1, 2, 3, 4).

The matrix is in one embodiment based on polyester fibres stabled into non-woven felt as manufactured e.g. by FiberTex A/S, Denmark or DelStar, Inc from the United States. Non-woven sheets can be cut, shaped into matrix sections that are essentially circular or has any other shape.

Non-woven sheet thickness can range from e.g. less than 1 millimeter to 150 millimeter or more, such as e.g. from 2 millimeter to 50 millimeter preferably between 5 and 25 millimeter. The fibre diameter can range e.g. from less than 0.1 µm to more than 1,000 µm, such as e.g. from 1 µm to about 100 µm or more likely from 5 to about 25 µm. The resulting packing density of a non-woven section is made of a material having bulk density preferably in the range of from 100 to 5,000 gram/dm$^3$ and a porosity ranging 50 to 99% of the non-wovenx material itself. Thus corresponding a non-woven fibre surface area ranging 50 to beyond 3,500 m$^2$ per liter non-woven or m$^2$ for a 10 millimeter thick matrix disc.

Two or more than two non-woven discs or sheets pieces may be stacked, thereby forming a matrix section, which matrix section can again be stacked in a multi matrix section set-up. The matrix sections in the stack of individual matrix sections can be the same or different matrix sections and the individual matrix sections can have the same or different properties. The same or different properties can affect e.g. properties such as gradient densities, or gradient fibre thickness through the matrix to obtain asymmetric matrix properties or just suitable thickness. Also, the individual fibre sheets or matrix sections can be manufactured with asymmetric pore size properties perpendicular to the individual fibre sheets.

Feeding liquid is diverted to the bio-reactor through an inlet port and initially enters a feeding tube in liquid contact with a plurality of individual matrix sections via a plurality of spacer sections capable of diverting feeding liquid exiting the feeding tube through a plurality of holes therein to the matrix section of the bio-reactor.

Liquid feeding medium is diverted at least partly and in some embodiment entirely by means of hydraulic forces through the matrix and comes into contact with the biological cells residing, adhered, suspended within the porous matrix sections. These matrix sections typically comprise at least one three-dimensional porous matrix having an open pore volume e.g. of from 15% to 99%, such as from 20% to 98%, for example from 30% to 90%, such as from 40% to 80%. The open pore volume, porosity is accounted for by open pores having an average diameter e.g. of from 1 to 500 µm, from 5 to 500 µm, such as from 10 to 100 µm. An open pore is defined by a pore capable of establishing a liquid connection with a multiplum of neighbouring pores said multiplum of pores defines a matrix between spacer sections located on opposite sites of an individual matrix section. Two such oppositely located spacer sections are termed corresponding or operable linked feeding spacer section and drainage spacer sections. The correspondence occurs when feeding liquid diverted to an individual matrix section by a feeding spacer (section) is subsequently—following passage of the matrix section in question—diverted away from the matrix section by a drainage spacer (section).

The size of the matrix sections is not limited to any particular diameter or surface area and in one embodiment the present invention is directed to matrix sections having a diameter of less than 1000 millimeter in diameter. Matrix section thickness may vary from a few millimeters to 250 millimeter, such as preferably less than 200 millimeter, for example preferably less than 150 millimeter, though a thickness ranging from 5 to 50 millimeter, such as from 10 to 30 millimeter is according to one presently preferred hypothesis believed to be more relevant.

The bio-reactor in one embodiment comprises a number of identical, or differently shaped, stacked matrix sections and has e.g. at least one central inlet and a circumferential outlet assembled in a fluid tight housing. However, the opposite orientation is also possible, i.e. a circumferential inlet and a central outlet assembled in a fluid tight housing.

The preferably non-woven matrix sections are separated by spacer sections for liquid flow distribution, i.e. for both feed and drainage of feeding liquid. Feeding spacers and drainage spacers are sealed in opposite ends, respectively, to achieve flow direction control. This design has been found to provide an extraordinary uniform deposition of the introduced (seeded) biological cells, such as micro organisms, and most important—the design has been found to provide a uniform flow distribution.

In the present invention, the individual matrix sections are stacked on top of each other and separated by spacers on both the inlet side and on the circumferential side. This design creates a symmetrical and parallel arrangement so that the spacers located between different matrix sections correspond with and, under practical circumstances, is in liquid contact with, both one or more inlet port(s) and one or more outlet port(s) which are isolated from the inlet port(s) and/or from the matrix sections by said spacers. The drainage spacer sections located on the "outlet side" of the matrix sections communicate with and are in liquid contact with a common collection volume e.g. located at the circumference, such as e.g. in a cavity of the encapsulation of the bio-reactor.

Nutrients and fresh media to the biological cells, such as micro organisms, are introduced into the bio-reactor via one or more inlet ports and pumped through the reactor constantly to the circumference exit of the reactor.

Preferably non-woven, porous matrix sections stacked and laminated with feeding spacer sections and drainage spacer sections provide as much as up to 20 to 100 times more surface area/porous volume to bio-reactor suspension batch volume. The example is a conventional, industrial stainless steel vessel having an internal diameter of 300 millimeter and a length of 1,000 millimeter and approx. 70 liter of volume. With matrix sections packed to 50% of the packing density (significantly more than 40 $m^2$/liter internal surface area) of a 140 liter container, the total surface area for semi-adhering or agglomerate micro organisms in suspension is an impressive 40×70=2,800 $m^2$.

The matrix sections is in one embodiment stacked around one or more centrally located feeding tube(s) which supplies feeding liquid comprising nutrients required for biological cell cultivation to the feeding spacers through a plurality of holes or openings or feeding liquid outlet port(s) located in said one or more centrally located feeding tube(s). The feeding spacer sections provide feeding liquid to the matrix sections which in turn ensure an optimised radial and orbital flow pattern of the feeding liquid. The centrally located feeding tube(s) can also supply oxygen and distributes the oxygen efficiently, thereby solving the gradient problems which are typically a limiting factor when performing bio-cultivations. The concept of stacking the individual matrix sections allows significant matrix diameters and matrix heights to be employed while at the same time having a control of feeding liquid distribution and drainage.

The matrix sections can also, in one embodiment, be covered by or surrounded by independent membranes based on thin sheets having a pore size less than that of the preferred, biological cells to be cultivated. The membrane(s) are alternatively mounted on the outlet side of each matrix section—thereby creating a pressure drop eliminating nutrient concentration gradients across the inlet matrix section side—and thereby eliminating such gradients from the entire matrix surface.

The matrix sections or cassettes comprising such sections can alternatively be assembled into a supporting base, a cartridge or a housing e.g. having a central inlet and a circumferential outlet. Such matrix sections can be fabricated from fibres of e.g. non-woven materials, polymers, ceramics, metals, and celluloses with or without an integrated, high pressure drop membrane.

Feed and drainage spacers can e.g. be a layer of flow-net, screens, corrugated sheets, netting, rib stiffener, set of ribs in general, set of ribs arranged randomly, set of ribs arranged symmetrically, section with a radial set of ribs having suitable (edge) flow characteristics=excellent liquid flow along and within the thickness of the spacer. Spacers may be layers of flow-nets, screens, porous rigid foam alike structures and corrugated sheets, nettings assembled with different properties creating an (a)symmetric structure. Hereby the pressure drop along the feed and drainage layer is considerably lower than the pressure drop perpendicular to and through the matrix. Materials may also be of hydrophobic character to avoid fouling, trapping of micro organisms.

Some extruded flat flow-net separators may have a first set of parallel strands and a second set of parallel strands intersection the first set of strand at an angle. And be extruded polymer mesh from companies like Nalle Plastics Inc or DelStar Inc or Industrial Netting Inc. all located in USA or Mallanet from Spain. Extruded flow-net are characterised by their thickness (range 0.1-4 millimeter), by the number of strands per inch (2-64), mesh per inch (mpi), hole size (0.2-50 millimeter) and open area.

Alternatively the flow-net may be expanded sheet materials made by a process of slit and stretch performed by Dexmet Corp in USA and characterised by the material thickness, number of strands per inch, strand width, mesh per inch (MPI), openings per $in^2$, and open area. Both flow-net examples corrugated for high flow capabilities and potentially laminated with flat and fine pored spacers on each side in order to avoid intrusion of the matrix core materials. In particular for FIGS. 1, 6, 7, such lamination method is highly suitable. FIG. 6 is a pleated type of design with the pleats arranged both curved and combined radial and symmetrical around the centre line from which spacers extent.

Alternatively, the spacer may be a cast, rapid prototype printed, moulded device round, rectangular, square or of any shape for lamination with the individual matrix sections. Examples include a round feed spacer e.g. based on a radial rib design thicker, higher at the feed entrance and thinner, lower closer to the collection volume entity. The drainage spacers are of the "opposite" design—i.e. thinner, higher at the feed entrance and thicker, lower closer to the collection volume entity.

Spacers preferably include seals, connections, mechanical support etc. for stacking purposes. Spacers can e.g. be cast bodies with rib design, channel design, pore size, material shape and choice with design specifically to be laminated with matrix sheets. Such as being part of description in FIGS. 2, 3, 4 and 5.

Flow net spacers could alternatively be designed with ribs and fluid flow paths suitable for integration during production of the porous matrix and hereby be fully embedded. The purpose is to simultaneously give mechanical support to the structure and act as either or both feed and drainage spacers for the fluid to pass the porous matrix of the embodiment. Fluid inlet and outlet in particular arranged at each end face and hereby different to known cylindrical pleated filters with inlet, outlet on the inner or outer surface of such a cylindrical body. The spacer hereby becomes a one time, single-use mould and by being embedded into the overall embodiment participates potentially optimum in the fluid distribution.

Flow net or similar structures may be integrated inside, embedded inside the non-woven matrix or between layers of woven matrix in order to obtain a specific rigid appearance. Such a design is seen from German Fortron named PPS with difference in fibre thickness of at least 1:10 preferably higher. Layers of non-woven and woven materials may further be oriented according to need and are not limited in any method of assembling.

Alternatively the spacers, or parts of the spacers, may be manufactured from natural vegetable organic materials for natural re-cycling purposes after its use.

In general, the physical dimensions of the spacer sections are determined by the size of the practical circumstances characterising a particular cultivation of biological cells. If the bio-reactor is manufactured with a large diameter, the feed inlet in operable liquid contact with a spacer section must be larger than a feed inlet in operable liquid contact with a spacer section when a smaller diameter bio-reactor is used.

One other embodiment of the present invention (version 2=envelope) features the variation of the bioreactor containing the packed bed material enclosed by porous walls such as defined as an envelope (FIG. 4). The envelope is preferably (but not limited to be) a rotation symmetrical, a circular box, container of trapeze alike cross section with at least a part of the sieving effect wall constituting a rigid or a flexible porous membrane with pores of a size suitable to retain the packed bed of growth bodies for a packed bed thickness of 5-250 millimeter, preferably ranging 8-150 millimeter such as 10-50 millimeter. The envelope walls, when based on porous sheet materials, flow, net sheets, textiles, sieves, fabrics or non-woven materials, may be connected at the inner and outer circumference like by various welded methods or sewed with thread, from various pieces of sheet into said envelope shape while integrating and fully inclosing the packed bed material. Two envelopes may share the same symmetrical feed spacer and by further joining the flexible porous membrane at least at the circumference of both envelopes, creating a stackable envelope unit by encapsulating the feed spacer. The envelope walls, such as a sieve or a membrane may be a polymeric material cast into shape or a pre-shaped sheet of polymeric based material with macropores or holes in said membranes or wall able to retain the packed bed material.

Alternatively the drainage spacer is encapsulated or both feed and drainage spacers are encapsulated. On the feed side of the envelopes, before the packed bed, spacer devices insure even radial flow pattern to the twin packed beds simultaneously. The envelope walls on the drainage side of the twin packed beds are next to a radial fluid collection volume, which continue the radial flow pattern from the twin packed beds simultaneously. The envelope membranes are in no way limited to have parallel walls or being of flat design. Multiple envelope bodies may be stacked inside a container a vessel or a disposable capsule.

Further one way of manufacturing such envelope bodies is by packing a suitable amount of powder mixture material and/or fibres into a casting mould offering some handling strength before the stack assembling. Or multiple porous packing bodies arranged randomly between the porous membranes creating an envelope before the membranes are fixed at the edges. Two such envelopes are arranged on each side of and share a non restricted central feed spacer. One such envelopes further shares drainage spacer as a non restricted common outlet with the neighbour envelope.

The bioreactor device with permeable envelope walls allow micro organisms to pass said walls and travel into the interior of the bioreactor envelopes. The growth bodies contained inside the envelope preferably have controlled specification combined with the required large surface area/ porous volume suitable for supporting micro organisms. If chosen the pores in the drainage membrane, down stream side of the envelope, may be of a different size compared to the feed membrane, which restricts both the growth bodies and partially the micro organisms from leaving the bioreactor envelope, but not the product. Or other desired function of the outlet membrane(s) may be obtained. Envelope dimension may range 1-1,000 millimeters in diameter, e.g. 10-1,000 millimeters in diameter, and an envelope unit height of 1-300 millimeters before stacking and feed and/or drainage spacer integration.

Further one embodiment of the present invention (version 3=pleated sheet into cylinder shape) is a pleated bio-reactor based on pleating of a non-woven sheet matrix into a compact reactor (FIG. 6). A pleat is a type of fold formed by doubling fabric, sheets backed upon itself and securing it in place. Pleating is a compact method of obtaining high loads of fabric, porous sheets and used extensively in the filtration industry and the manufacturing method is often called knife pleat. If order to avoid each pleat gets in contact to the neighbour pleat separators, spacers with fluid capability are arranged between the pleats. The pleat matrix thickness is selected in order to get the desired flow and pressure drop over the matrix. The pleat will typically be of the same thickness all through the core. The pleats are typically arranged on the straight radial lines of the cylindrical core though higher pleat density is obtained if the lines are curved and not starting from the core centre. Two individual diameter pleated bodies may be arranged into the same housing with one pleated body surrounding the other with the upstream volume shared, being in between the two bodies so one downstream becomes the centre of the in diameter smaller body and the other downstream the circumference of the in diameter larger body. Module dimensions ranging 50-500 millimeter in diameter with length of 200-2,000 millimeter though preferable 500-1,000 millimeter in length.

Feed and drainage spacers can e.g. be a layer of flow-net, screens, corrugated sheets, netting, rib stiffener, set of ribs in general, set of ribs arranged randomly, set of ribs arranged symmetrically, section with a radial set of ribs having suitable (edge) flow characteristics=excellent liquid flow along and within the thickness of the spacer. Spacers may be layers of flow-nets, screens, porous rigid foam alike structures and corrugated sheets, nettings assembled with different properties creating an (a)symmetric structure. Hereby the pressure drop along the feed and drainage layer is considerably lower than the pressure drop perpendicular to and through the matrix. Materials may also be of hydrophobic character to avoid fouling, trapping of micro organisms.

In another embodiment of the present invention (version 4=spiral-sheet into cylinder shape) a spiral bio-reactor being of cylindrical and elongated design with a series of parallel oriented dual spiral layers of non-woven matrix sheets laminating the drainage channel spacers and on each side in contact with the feed channel spacers all wound around a central perforated fluid collection tube (FIG. 7). The drainage spacer is shorter and less wide than the matrix sheet and on three sides sealed from the feed stream with seals between and/or bonding of the matrix sheet edges, which hereby form an envelope around the drainage spacer, though the drainage spacer is open to, connected to and in unhindered permeate fluid correspondence with the perforated fluid collection tube. The feed spacers are open on all four edge sides and with no fluid connection to the fluid collection tube receiving the permeate. Anti-telescopic members are mounted at both end surfaces of the sandwich like circular core matrix.

Typically operating in cross-flow mode with longitudinal flow, the feed are supplied from one end face being conveyed in axially direction inside the coarse and somewhat thick feed spacers to the opposite end face exiting as retentate. A slight over pressure drives the fluid perpendicular to and through the matrix core collected on the other side of the matrix by the drainages spacers conveying the permeate fluids tangential to the central collection tube where the drainage spacers are anchored. The element is to be fitted inside a low pressure container being fabricated from rigid or flexible materials. More than one element may be fitted into the same container in series, after each other and share the central collection tube permeate fluid exit. Alternatively the core is not fitted tight inside a tube, but with free feed or head space around the core circumference and in longitudinal direction allowing the feed stream to enter the feed spacers perpendicular to the core.

Feed and drainage spacers can e.g. be a layer of flow-net, screens, corrugated sheets, netting, rib stiffener, set of ribs in general, set of ribs arranged randomly, set of ribs arranged symmetrically, section with a radial set of ribs having suitable (edge) flow characteristics=excellent liquid flow along and within the thickness of the spacer. Spacers may be layers of flow-nets, screens, porous rigid foam alike structures and corrugated sheets, nettings assembled with different properties creating an (a)symmetric structure. Hereby the pressure drop along the feed and drainage layer is considerably lower than the pressure drop perpendicular to and through the matrix. Materials may also be of hydrophobic character to avoid fouling, trapping of micro organisms.

Compared to the typical and in the industry well known spiral wound membrane filter, which need to fulfil high demands to trapping efficiencies, the spiral-bio-reactor has low demands to filtration efficiency. Module dimension ranging 50-250 millimeter in diameter and length 200-1500 millimeter preferable 100-500 millimeter.

According to further embodiment of the present invention (version 5=cast bodies) is a rigid foam based porous matrix structure. The foam alike, scaffolding and permeable bodies may take any shape, thickness as discussed in other parts of the present invention. Such as discs shaped, plate shaped, saucer shape, honeycomb shaped. Be single and double density biopolymer foams, composite biopolymer foams including both single and double density foams. The foam alike scaffolding may be cast or 3D printed or manufactured by stereolithography methods.

Solid foams form an important class of lightweight cellular engineering materials. These foams can be classified into two types based on their pore structure. The first type of foams is called open cell structured foams. These foams contain pores that are connected to each other and form an interconnected network which is relatively soft. The second type of foams does not have interconnected pores and are called closed cell foams.

The foam may be semi rigid or soft bodies based on pure natural sponges from the in sea living marine organism such as *Spongia officinalis*, or fresh water sponges like *Spongilla lacustris*.

Foam structures based on traditional manufacturing methods where polyurethane foam are exposed to and impregnated with a ceramic fine grained slurry followed by drying and high temperature firing. Specification of the hereby negative skeleton are typically with a maximum of 100 ppi (pores per inch) corresponding to pores as small as 0.5 millimeter in diameter.

A new and promising process for fabricating ceramic foams or calcium phosphate containing foams pass a route of stable, well-dispersed, high solids content, aqueous ceramic suspension is prepared which also incorporates an acrylate monomer together with an initiator and catalyst. The latter is used to provide in-situ polymerisation. After the further addition of a foaming agent, a high shear mixer is used to provide simple mechanical agitation that result in the formation of wet ceramic foam that can be dried and then fired. Foams can now be produced with largest pores 1 millimeter and densities as high as 30% of theoretical, whilst 20% dense foams have been produced with pores as small as 20-50 μm. Bio ceramic containing foams are known for promoting cell growth and being bio friendly in the bio medical industry.

According to another embodiment of the present invention is a body (version 6=cast bodies) with a set of inlet channels and outlet channels. Traditional honeycomb bodies are all characterised by thin walls with limited wall porosity and channels as small as possible measured in CPSI—cells/channels per square inch—being in the range of 100 to 600 cpsi. In specific traditional flow-through honeycomb bodies are designed only for fluid flows along the channel and not trans/through the wall—and in specific not for growing micro organisms within the wall matrix pores. One embodiments of the present invention is a honeycomb body which differs vastly from traditional honeycombs exhibiting unusual thick walls and wide channels and high internal surface area within the wall matrix pores highly suitable for biofilm attraction. Also the present invention takes advantage of the Wall-Flow-Filter principle. The media, fluid passing through the bioreactor differs from known technology as the fluid, the medium is passing through the wall matrix. Furthermore the media flow through such bioreactor preferably sees a relatively higher pressure drop when combining a membrane with said porous wall matrix. As the added membrane with significant higher pressure drop support an even fluid flow all over the inlet wall surface area. The reduced nutrient content gradient improves the yield of the present invention significantly. Pore size in the three-dimension matrix operating as a the invented bio-reactor ranging 1-500 μm preferably 10-50 μm creating 10-100 m² internal wall surface area per liter matrix. Porosity ranging 30-98% in the matrix if the said bio-reactor is fabricated from grain particles though often with practical porosity ranging 40-60%. The coarse matrix gives permeability ranging 0.1-10 Darcy preferably closer to 1-5 Darcy. Also it is very advantageous to have thick walls for optimum internal surface area such as FIGS. 8 and 10.

Otherwise the wall thickness may be e.g. 1-150 millimeter, preferably 5-50 millimeter. The cell pitch, which is the combined measured figure in millimeters of the wall thickness and the channel width, may be in the range of 1-75 millimeter, preferably 5-30 millimeter. In one embodiment the bio-reactor will in a single body designed with 0.1-10 cpsi (cells per square inch) configuration and outer dimension of OD144×L152 millimeter offer the volume of ~2.4 liter. For the conical channel cast version cell density may range from 0.1-5 cpsi with non circular channels. Bodies like FIG. 10 are not known in the industry and not measured via cells per square inch.

A significant feature of the present invention is the three-dimensional very thick porous walls to which potentially membranes are adhered. Conventional wall-flow-filter or cross-flow-filtration devices preferably have very thin walls in order to minimise wall and/or trans-membrane pressure drop. A pressure drop comparison between the high volume flow wall-flow-filter and cross-flow-filtration with the present invention reveal difference.

One way of manufacturing such rigid carrier body is obtained by pressure casting, vacuum casting or casting supported by vibration or pressing particles into the desired shape followed by sintering a bi-modal powder mixture comprising coarse-grain material and a fine-grain substance melting at a higher-than-sintering temperature gluing the coarse grains together in the contacts points.

Alternatively ways of manufacturing such rigid carrier body is obtained by casting or pressing mono-modal particles into the desired shape followed by sintering the powder mixture at higher-than-melting temperature gluing the grains together in the contacts points.

The channels of the typical extruded honeycomb body are limited to exclusively parallel wall design as obtained from the extrusion process. Better gradient eliminating design is obtained by conical channels with larger free end face openings and conical walls towards the end of the particular channel, but such design needs to be cast, slip cast, pressed, vacuum cast, etc. The design in order to optimise, exclude environmental gradients along the channels and through the channel separating walls. Both the feed and drainage channels being conical along the body may be round, square, hexagonal, octagonal or any other shape which offer identical wall thickness anywhere in the body. Further both the feed and drainage channel form may be mixed into any desired design.

According to further embodiment of the present invention is porous discs (version 7=cast bodies) with pore size in the three-dimension matrix ranging 1-500 μm preferably 10-50 μm. Porosity ranging 30-98% in the matrix if the bio-reactor is fabricated from fibres, often practical porosity ranging 40-90%. The discs arranged towards each other in sets forming feed spaces and drainage space as illustrated in FIG. 4. Cast from either powder based material or from fibre based materials or both combined. Assembling sets of the discs by stacking create the bio-reactor device to be housed in a standard stainless steel dome covered system with bottom plate which contains inlet and outlet. If manufactured from fibres methods are known under the names knitting, weaving, and braiding potentially followed by a gently sintering process, which increase mechanical strength of the discs. Also mixing of metal fibres with organic fibres is known as multifilament yarns in the industry. Such multifilament yarns will give interesting properties with partly electrical conductivity allowing selectable charging of the mesh.

One further embodiment of the present invention is a body (version 8=cast bodies) with a set of inlet channels and outlet channels manufactured by vacuum forming, such as when a porous mould is exposed to, dipped into a volume of and in contact with a suspension including flocculated fibres. Low pressure on the back side of the perforated surface convey the carrying suspension, slurry to flow towards and through the mould where the fluid are drained through the porous screen, retaining the fibres which is collected and deposited on the mould surface. Exposure time to casting, suspension strength determine the thickness of the accumulated fibrous matrix body on the mould surface. After the vacuum casting process the body is removed and the remaining fluid is finally removed by drying and the body appear semi rigid. Typically a binder system is mixed into the suspension in order to facilitate anchoring the fibres internally for higher product stiffness. The initial vacuum casting process may be followed by further similar process in order to obtain asymmetric matrix properties. The matrix may for improved mechanical strength include a skeleton of pre-shaped thicker fibre or thread based mesh arranged prior to the vacuum casting process so the mesh becomes fully embedded in the structure after the vacuum casting process.

Further ways of improving mechanical strength after the vacuum casting method is possible by adding resins or by heat treatment. Such heat treatment may further shrink the body hereby reducing the pore size.

Making up such body will follow the alternative procedure, which is here described with particular reference to the embodiment illustrated in FIG. 4 and FIG. 8, 10 by uni-axial pressing such as when a set of moulds is exposed to a fluid suspension containing at least one type of fibres and possible binders and/or resins. A suitable volume of the suspension is allowed to flow into the casting cylinder for uniform settling containing at least one mould pistons. The suspension may be kept floating by gas introduced added from the bottom piston in order to improve suspension uniformity. The gas added under pressure from a series of holes in the piston or cylindrical wall. After filling the open casting chamber with suspension the top mould piston is moved into, closing the cylinder. At least one of the mould pistons is manufactured from macro porous materials, perforated or supplied with a multiple small drilled holes or variations thereof, which allow the suspension fluid passes out through the two pistons. While forcing the two pistons towards each other the fibres left in the cylinder is orienting and compacting to an embodiment of desired design. After the moulded article has obtained final shape the soft felt embodiment is removed from the casting machine and the remaining fluid is removed by drying until the body appear semi rigid.

Typically a binder system is mixed into the suspension of fibres in order to permanently anchor, adhere, bond the fibres at their contact points for higher embodiment stiffness. Alternatively the semi finished matrix embodiment after casting is further impregnated, exposed to a binder system dispersed, diluted in an aqueous solution for a soaking time based on wall thickness. The binder system may be cured by temperature, UV lights, reacting with a catalyst, etc. bonding the fibres together.

Pore size in the three-dimension matrix ranging 0.001-500 µm. For depth filter applications the pores range 0.01 to 100 µm pore size. For bio-reactor purpose the pores are preferably 10-100 µm creating 10->250 m² internal wall surface area per liter matrix. Porosity is ranging 40-98% in such matrix and if fabricated from fibres of various spec, often practical porosity range 60-98%.

The above variation of the present invention is only limited in dimension by manufacturing restrictions. Parts of the above may be sandwiched in order to obtain combined properties. Any of the above embodiments may have asymmetric pore structure carried out by methods well known in the industry.

Organic membranes—the possible extra membrane(s) mounted on the outlet side of the matrix outlet surfaces which hereby create further pressure drop. This effort in order to further reduce nutrient concentration gradients across the matrix and in specific the surface of the entire three-dimension matrix. The micro organisms hereby gets trapped inside the three-dimension matrix before the membrane(s) creating a biotech growth method for continuous protein expression and micro organism separator in just one system.

Outlet membrane with pores ranging selectively insures the cells, micro organism or biofilm do not penetrate the growth body, but only the product and nutrient pass the membrane mounted on the drainage side. The membrane(s) permeability is in the range of 1-100 times less than the three-dimension matrix being the wall. The membrane is designed from particles and/or fibres creating a smaller pore size than the growth body and applied on the fluid outlet side surfaces of the carrier body with macro pores, the membrane having pore diameter of 0.001-20 µm. Typically, such membrane is required when separating or allowing very small particles or suspended matter only to pass the membrane attached to the inlet side of the carrier. For the present invention the purpose of the membrane is opposite and works backwards as the membrane is attached to the outlet, drainage side which prevents release of anchored particles or cells oriented carefully inside the porous matrix—and only the product from the cells are allowed to pass the membrane. This principle is advantageous as the micro organisms are not removed from the interior of the carrier body.

In-organic membranes—the honeycomb and cast body design of the invention may be combined with a separating micro porous membrane(s) for selective passage of particles and fluids. The possible extra membrane(s) mounted on the outlet side of the matrix outlet surfaces and hereby created pressure drop eliminate nutrient concentration gradients across the matrix and the entire three-dimension matrix surface. The micro organisms hereby trapped inside the three-dimension matrix before the membrane(s) creating a biotech growth method for continuous protein expression and micro organism separator in just one system.

Outlet membrane with pores, holes ranging selectively from 5 to 10,000 nm sizes insures the cells, micro organism or particles do not penetrate the body, but only the product and nutrient does. The membrane(s) permeability being in the range of 1-100 times less than the carrier, the three-dimension matrix of the wall. A membrane may be designed from particles or fibres creating a smaller pore size than the growth body and applied on the fluid outlet side surfaces of the carrier body with micro pores having a diameter, size of 0.001-10 µm. The asymmetrical membrane applying a pressure drop being at least one order of magnitude higher than the pressure drop obtained from the carrier. The membrane material selected may be determined from its Zeta potential. Some materials like Zeolites may easily be altered. Membrane with pore sizes smaller than pores of the carrier body material deposited on the membrane carrier increases the separation efficiency of the device. This membrane also prevents particles from exiting the porous carrier. Typically, such membrane is required when separating or allowing very small particles or suspended matter only to pass the membrane. For the present invention the purpose of the membrane is opposite and works backwards—the outlet, drainage side mounted membrane prevents release of anchored particles or cells oriented carefully inside the porous matrix—and only the product from the cells are allowed to pass the membrane. This principle is advantageous as the micro organisms are not removed from the interior of the carrier body.

Hereinafter, the term "ceramic bio-reactor device" encompasses a porous monolith support for both the active micro organisms as well as potentially the membrane device and then the term "bio-reactor" encompasses permeate extracted from a membrane device. Such membranes can include separation barriers suitable for micro-filtration, ultra-filtration, nano-filtration in order to be selective to the inclusions in the permeate.

Bio-reactor Design

The invention is not limited by dimensions or in any way to a symmetrical shape. The core may be of non cylindrical design, inlet volume shape or outside shape may be independently different with non parallel sides, trapeze design as yet an input for flow distribution control and gradient elimination. Asymmetrical porous matrix assembly with decreasing pore size perpendicular to the disc may further be combined with the shape for flow distribution control purposes. Permeable bodies, discs or envelopes with different properties, different materials may be stacked in any order and thickness.

When the invention is designed into a disposable plastic container construction the container may further house a heating element or temperature conditioning devise as well as appropriate sensors. A heating element may also be located within the inlet volume fully surrounded by the fluids to pass the core. In large bio-reactor systems the heating elements may further be oriented within the spacers preferably be integrated with the inlet zone spacers.

Fluid Analysis work has been performed with the CAD computer program SolidWorks® fluid analysis tool Flow-Works on powerful Intel® workstations in order to finally design the spacer shape (25a, 25b) and matrix (21) dimensions. The result is a flux with less than 5% variation over the entire matrix feed surface and the FIG. 2 design is specifically a result of such work performed by Stobbe Tech A/S in Denmark.

Housing Design

The bio-reactor permeable bodies is preferably enclosed inside a container made by bio compatible polymers, plastics as housing with connected silicon or plastic hoses and/or flanges. The plastic container enclosure is an alternative design with the purpose of being disposable and of a relatively low cost. The plastic container or bag may be semi rigid as the reactor is both compact, but also of fixed dimensions and rigid. With a tight fit for the plastic film bag around the matrix core the complete set-up becomes self supportive and need no extra external support like empty single-use plastic bags, which all need a rigid container as support. The plastics selected should offer low levels of leachable and extractable compounds. Plastic film sheets formed into desired size, shape and by one or several of various welding methods seamed at the edges into a liquid tight container around the bioreactor.

More rigid plastics based capsules systems, self supportive design will allow for stacking purposes and may on the outside appear symmetrical and the core on the inside may be asymmetrical. Stacking will arrange the capsules next to each other with inter-connecting fluid exchange flanges sealed insuring liquid tight performance. Improved mechanical strength for plastic parts is well known in the industry by adding fibres to the hot plastic during forming. Also electrical properties can be altered by specific substances added to the polymers.

The disposable capsules may be of tangential flow principle, radial flow principle, cross flow principle with symmetric or asymmetric porous matrix core design and either of round design, rectangular or combinations hereof.

Yet a variation is non round capsules or cassettes with at least one fluid inlet and at least one fluid outlet integrated within the capsules overall design. Such as the Plate & Frame design, an expression for old fashion assembling of a larger number of cassettes into a holder system with the typically square or rectangular plates operation typically in parallel. Also known as "filter presses" or "membrane plate filters" in the industry. A very common principle in the filtration industry and the design, column principle may be used for the present inventions bio-reactor.

The ceramic and metal based bio-reactor permeable body is extremely tolerant around the cleaning issue. Sterilization may be performed with steam, high temperature exposure like 500° Celsius and exposure to warm fluid in the pH range of 1-14 pH. The bio-reactor permeable body mounted in a housing manufactured from stainless steel or plastics suitable for fluid tights assessment and with mechanical strength for enclosure.

Sensor Integration

On-line measuring of $O_2$, pH, temp, $CO_2$, glucose, lactate, flow, cell mass, pressures, etc. for understanding and perform the process control is mandatory for optimum metabolism in the bio-reactor. Any of the inventions variations may include passageways incorporated for correspondence with traditional 12 millimeter sensors, probes for monitoring. Sensors as supplied from Hamilton, Mettler, Fogale, Finesse etc. with Pg13.5 thread are used in the industry and inserted in ports via sealed connections being twisted open during insertion.

It is preferable to use single-use sensors as to the fact that the industry shift to disposable bio-reactors bags, as to this the need for disposable sensors becomes important and a significant improvement. The above invented bio-reactor core arranged in a bag of flexible materials or in cassettes, containers, capsules or the like from non flexible materials allow the bio-reactor to be single-use and disposable. It is advantageous to avoid introduction of any foreign articles such as standard 12 millimeter diameter sensors, probes, transmitters after bio-reactor sterilization. And such sensors will not accept the sterilization or they loose their calibration. Relevant real-time sensors are such as for measurements of gases, dissolved gases, liquids, temperature, cell density, organics, pressures, etc.

The present invention in one embodiment do benefit from disposable sensors being integrated into the bio-reactor bag, containers or capsule. Sensors have the advantages that they can be engineered to be non-invasive or introduced into the bio-reactor before gamma sterilization occurs, generally do not have stringent grounding requirements, and can often provide enhanced performance over existing chemical or electrochemical methods. A variety of sensors principles are used; chemical-optical, optical, fluorescence, near infrared spectroscopic—NIR, Partial Least Squares—PLS, Principal Component Analysis—PCS, radio frequency, impedance, capacity, capacitance or others.

Compact single-use sensors are manufactured by the German company PreSens Precision Sensing GmbH being flat to less than 0.1-5 millimeters, less than 50 millimeter in diameter. The sensor elements are attached to the inside of the bio-reactor container corresponding through the translucent container wall material to a transmitter on the outside for non-invasive and non-destructive operation. An alternative product is from Finesse Corp from USA who offers a line of disposable optical sensors for detection of dissolved oxygen and pH.

Operation Modes

Perfusion mode operation of a bio-reactor allow for continues expression and hereby constant harvest. The bio-reactor is operated in a configuration with at least one inlet and at least one outlet. The majority of the media volume is passing the matrix being re-circulated in orbital motion rotational symmetrical around the bio-reactor centre continuously. A suitable flow is taken out continuously including the expressed product and processed separately. A similar volume is added as fresh nutrient to control metabolites concentrations. Alternatively the expressed product is harvested separated from the used media discharge which is drained separately. A fresh media volume is added corresponding harvest volume and used media drained volume in order to keep a constant media volume and nutrients level inside the bio-reactor. The harvested and desired product may be filtered inside the bio-reactor or directed to the down-stream processing. Filtering for separation of cells, cell debris or the like. Such as re-circulation of cell suspended in the harvest fluid stream and further in the used media drainage.

Fresh media may be selected advantageous to supply with selected concentration levels of various nutrients according to the process. Used media may be re-cycled external of the bioreactor and re-used in said bio-reactor after removal of lactate or metabolism bi-products in general.

Flow speed, liquid velocity, flux of the media passing the porous matrix of the invention perpendicular to the permeable bodies should be in the range of 0.01-200 cm/min preferably 0.1-50 cm/min, e.g. 0.1-25 cm/min. Measured per $cm^2$ and perpendicular to the permeable bodies inlet surface. Too high media velocity will not allow the micro organism to be stationary inside, colonise the entire matrix and to low media velocity will not supply sufficient nutrient and oxygen to keep the micro organism healthy and productive.

Cross-flow (or tangential-flow) operation gets its name because the majority of the feed flow travels axially along the matrix core centre, rather than perpendicular across the matrix. The reactor feed fluid flow volume is significant larger than in pure perfusion mode. The technology offer continues expression and constant harvest as the advantage. In cross-flow mode the bio-reactor is operated in a configuration with one inlet and two fully independent and separated outlets. The feed flow volume to the reactor is the combined retentate (fresh nutrient passed the reactor unused) and the permeate (used nutrient including product) flow. The advantage is unlimited individual adjustments of the three flows, which controls accurately:

1. the feed flow through the matrix (containing the micro organism) and
2. the reactor operating pressure and 3. equally important the retentate flow of fresh nutrient all along the inlet volume in the bio-reactor eliminating gradients Factors, which insures that any individual porous matrix bodies receive equal nutrient flow for elimination of gradients in each individual porous matrix cores. Cross-flow operation also allows precise control of the fluid shear forced in order to avoid removal of adhered cells from matrix surfaces. As no head space is needed and dissolved oxygenation is selected (no bubbles or sparging) outside the reactor the foaming problem is eliminated.

Growing and expanding tissues in vitro from donor cells require four components: Stem cells, a scaffolding made of polymers, a bioreactor and cytokines such as polypeptides that bind cell specific receptors in the cell membranes of target cells to trigger a response. The process involves seeding, loading and cultivation of the biodegradable scaffold with cells and cytokines and expands the cells in the bioreactor. The loaded scaffold may be removed as is or the cells removed from the scaffold and finalised by cell assembling to engineered simple tissues such as skin, bone and cartilage or complex shaped body spare parts, organs by 3D printing or Stereolithography methods.

Human Made Semi Synthetic In-organic Powder Materials

An alternative material for rigid matrix bodies (either for use as bioreactor or separation reactors) is by copying the human and animal material bone which consists of a biopolymer matrix (collagen) reinforced with mineral nano particles (carbonated hydroxylapatite), forming a natural composite which builds up a dense shell on the exterior and a network of struts with a mean diameter ranging 200 µm in the core of many bones. Bio ceramic hydroxylapatite (naturally occurring white mineral, calcium apatite (CaOH) with the formula $Ca_5(PO_4)_3(OH)$) and calcium phosphate containing bodies are known for promoting cell growth and being bio friendly. Used for more than a decade in dentistry and reconstructive surgery in the bio medical industry it is well known that hydroxylapatite based foams are highly suitable as matrix for cell growth. There are several approaches; such as rapid prototyping methods, ceramic gel casting and sintering to produce cellular structures with designed architecture from hydroxylapatite and other bio ceramics.

One way of manufacturing ceramic rigid large size carrier bodies is obtained by sintering a powder mixture comprising coarse-grain material and a fine-grain substance melting at a lower-than-sintering temperature gluing the coarse grains together in the contacts points. Produced from the bi-modal grain principle (coarse SiC grain F150 powders (~82 µm size) according to FEPA standards mixed with fine micro grained SiC FCP-15 (less than 1 µm size) both from French company Saint Gobain. The carrier with packed particles will have the surface area of app 20 $m^2$/kilo grain. And for OD144×L152 millimeter—2.4 liter body at total 4 kilo×20 $m^2$/kilo=~80 $m^2$ internal surface area. For the comparison a 20 liters body will hold 20×2.4 kilo/liter×20=960 $m^2$ surface area. Such bodies are though not disposable but will handle sterilization unlimited as to their chemical inertness. Silicon Carbide and Mullite has compared to Alumina, Zirconia and Titania the advantage to accept manufacturing in larger diameters and lengths.

An alternative material for rigid matrix bodies is by copying the human and animal material bone which consists of a biopolymer matrix (collagen) reinforced with mineral nano particles (such as carbonated hydroxylapatite), forming a natural composite which builds up a dense shell on the exterior and a network of struts with a mean diameter ranging 200 µm in the core of many bones. Bio ceramic hydroxylapatite (naturally occurring white mineral, calcium apatite (CaOH) with the formula $Ca_5(PO_4)_3(OH)$) and calcium phosphate containing bodies are known for promoting cell growth and being bio friendly. Used for more than a decade in dentistry and reconstructive surgery in the bio medical industry it is well known that hydroxylapatite based foams are highly suitable as matrix for cell growth. There are several approaches; such as rapid prototyping methods, ceramic gel casting and sintering to produce cellular structures with designed architecture from hydroxylapatite and other bio ceramics.

Fibres in General

Any fibre from natural or artificial origin, which is capable, by itself or through further treatment, of adhering micro organisms on its surface or support mobilised micro organism in pores, may be utilized. The material should be defined by several criteria:

1. tensile strength for processing the fibres into a 3D matrix structure
2. essentially insoluble in a neutral aqueous solution within a reasonable time
3. no release of substances, extractable into the aqueous media
4. bio compatibility with relevance to the specific micro organism
5. surface properties by nature or by treatment suitable for micro organism attachment Fibres may take shapes different from being round and solid, such as star shaped, square, octagon, triangular, hollow and their combinations.

Human Made Metal Fibres

Metal fibre with thickness of 1-50 µm are further suitable as raw materials for the here presented invention, design and manufacturing methods. Either drawn fibres or fibres cut or planed from solid materials into fibres such as the product Bekipor or Bekinox available from the Belgium company Bekaert. Typically the fibres are alloyed from at least elements like; ferrum, chromium, nickel, aluminium and preferably small parts of rare earth elements. Other selections from the elements and alloys may serve the task of attracting the micro organism. If the porous matrix is fabricated from metal fibres then porosity range from 50%, such as from 80% and higher than 90%.

Human Made Synthetic Organic Fibres

Synthetic fibres are the result of extensive research by scientists to improve upon naturally occurring animal and plant fibres. In general, synthetic fibres are created by forcing, usually through extrusion, fibre forming materials through holes (called spinnerets) into the air, forming a thread. Before synthetic fibres were developed, artificially manufactured fibres were made from cellulose, which originates from plants. Polyester is a category of polymers which contain the ester functional group in their main chain. Although there are many types of polyester, the term "polyester" as a specific material most commonly refers to polyethylene terephthalate (PET). Polyesters include naturally-occurring chemicals, such as in the cutin of plant cuticles, as well as synthetics such as polycarbonate and polybutyrate. Polyester is like all artificial crude oil based fibre materials hydrophobic, but the least hydrophobic and with less hydrophilic alike behaviour compared to than polypropylene. Biodegradable (aliphatic) materials (bio plastics), e.g. polyester fibers, generated from agro resources sees increasing interest and may be the future for the disposable bio-reactors, such as polylactic acid and polyhydroxyalkanoates.

Polyester is a category of polymers which contain the ester functional group in their main chain. Although there are many types of polyester, the term "polyester" as a specific material most commonly refers to polyethylene terephthalate (PET). Polyesters include naturally-occurring chemicals, such as in the cutin of plant cuticles, as well as synthetics such as polycarbonate and polybutyrate. Polyester is like all artificial crude oil based fibre materials hydrophobic, but the least hydrophobic and with less hydrophilic alike behaviour compared to than polypropylene. The basic product is melt blown fibres or yarn cut into desired length and with thousand of needles from each side of a belt of fibres machining the fibres into a fabric called non-woven.

Biodegradable (aliphatic) polyester fibers (bio plastics) generated from agro resources sees increasing interest and may be the future for the disposable bio-reactors, such as polylactic acid and polyhydroxyalkanoates based.

Organic, Vegetable Natural Grown Biological Fibres

Vegetable fibres are generally comprised mainly of cellulose: examples include cotton, jute, flax, ramie, sisal, coconut and hemp. Cellulose comes in several variations and the fibres serve world wide in the manufacture of paper and cloth. Cellulose in general offer hydrophilic behaviour and the fibres may be further categorized into the following:

Seed fibre: Fibres collected from seeds or seed cases. e.g. cotton and kapok

Leaf fibre: Fibres collected from leaves, e.g. sisal and agave.

Bast fibre or skin fibre: Fibres are collected from the skin or bast surrounding the stem of their respective plant. These fibres have higher tensile strength than other fibres. Therefore, these fibres are used for durable yarn, fabric, packaging, and paper. Some examples are flax, jute, kenaf, industrial hemp, ramie, rattan, soybean fibre, and even vine fibres and banana fibres.

Fibre: Fibres are collected from the fruit of the plant, e.g. coconut (coir) fibre.

Stalk fibre: Fibres are actually the stalks of the plant. E.g. straws of wheat, rice, barley, and other crops including bamboo and grass. Cellulose from trees, wood is also such a fibre.

The most used natural fibres are cotton, flax and hemp, although sisal, jute, kenaf, and coconut are also widely used. Hemp fibres are mainly used for ropes and aerofoils because of their high suppleness and resistance within an aggressive environment. Hemp fibres are, for example, currently used as a seal within the heating and sanitary industries and as part of composites for the automobile industry.

The use of cellulose materials as supports for immobilization of small molecules, proteins, and cells has received considerable attention for many years and possible applications have been pursued extensively. Chemically, cellulose is composed of β-D-glucopyranosyl units linked by (1→4) bonds and with additional inter chain interaction through hydrogen bonds, some of which form the so-called elementary fibrils. Elementary fibrils contain highly ordered crystalline regions and more accessible amorphous regions of a low degree of order. Cellulose is available in many different physical forms, such as fibres, micro granules, micro crystals, beads, gel particles, capsules, and membranes. Less pure cellulosic materials are used in industrial processes in the form of ropes, pulps, chippings, cloths, and paper.

Surface properties such as the Zeta potential defines the electrical charge on particles and surfaces, or charge at the double layer surrounding the particles, in aqueous suspension and may be measured with a Zeta potential meter by means of known electro-foresis or flow of sedimentation potential measurements.

The inventive step in this context is therefore to measure the zeta potential of the suspension or solution, which is going to be in contact with the substrate material and thereafter establish a proper coating, if necessary on the substrate in order to adhere the particles or micro organisms to the surface during growth. Recycling or cleaning of the matrix surface is then performed either by changing the pH-value of the suspension or by applying a suitable voltage or charge on the surface while cleaning the substrate.

TABLE 1 the pH of isoelectric point at 25° C. for selected materials in water are:

| Metal oxides | Formula | Isoelectric point at pH | Reference |
|---|---|---|---|
| Vanadium oxide | $V^2O^5$ | 1-2 | 3 |
| Silicon oxide (silica) | $SiO^2$ | 1.7-3.3 | 2 |
| Silicon carbide | SiC | 2-3.5 | 2 |
| Zirconium oxide (zirconia) | $ZrO^2$ | 4 (−11) | 2 |
| Glass | | 2.1 | 5 |
| PP, PET, HDPE, PVC | | 3.5-4 | 5 |
| Polyester | | 3-4 | 6 |
| Gelatine | | 4.9-9.4 | |
| Borosilicate glass | | <7 | 6 |

Every surface of a material has a tendency to adsorb electric charges. The electrical state of a surface depends on the spatial distribution of free charges in its neighbourhood. The Zeta potential is a very important factor for the attraction of micro organism to the offered surface inside the porous matrix. Via selection of the correct materials it is possible to design the surfaces to be more or less micro organism adhesion friendly. If the base carrier materials are selected from a material type not really suited for anchoring the micro organisms, then an ultra thin surface treatment with more suitable materials or charge is one way of designing the surface properties according to the needs. One example being that a re-crystallized Silicon Carbide grain based wall-flow carrier with relative low Zeta potential may be modified via a surface coating with a Zeta potential more suitable by an ultra thin $TiO^2$ or Zeolite coverage. Such coating thickness ranging from a few nano meters to a few microns.

Typically Zeta potential range for micro organism culture support should be between 7.2 to 7.4 for mammalian micro organism (like CHO) culture, 6.2 to 6.4 for Sf-9 insect cells, and 6.4 to 6.5 for Hi-5 cells. And in general pH gradient should be reduced or eliminated being a feature of the present invention. According to the selected micro organisms surface properties determined by hydrophilic or hydrophobic actions must be taken into account. And different surface properties within the same container should be selected careful. Polyester fibres are typically less hydrophobic or become easier wetted, more hydrophilic so to speak, compared to the more hydrophobic materials like polypropylene.

Surface coating, of fibre surfaces, grain surface, membranes surfaces and matrix surfaces with Extra Cellular Matrices (ECM) promotes micro organism semi-adhesion and agglomeration. Such absorbent as organic matters like peptides, proteins, amino acids, such as the artificial molecule poly-L-lysine or the protein product Alginate, Matrigel, Collagen, Fibronectin, Laminin or fibroblast or gelatine suspension as coating supporting becoming more hydrophilic for the micro organisms to anchor faster, give higher level of affinity.

The cell agglomeration within the pores of the non-woven polyester based matrix will benefit from pre-treatment of washing with methanol or ethanol followed a plasma torch, corona field treatment. Potentially sterilized under a UV light and alternatively immersed in a solution of 100 µg/mL poly-D-lysine and finally rinsed with sterile water.

Some Biomimetic materials offer even stronger electrostatic attraction than the amino acids (like poly-L-lysine) such as the laminin family containing the protein domain isoleucine-lysine-valine-alanine-valine (IKVAV).

The examination of micro organism, stem cells, living cells being semi-adherent of in suspension is a large scientific discipline. Usually, manufacturers use inexpensive materials like synthetic polymers or glasses, which easily can be formed in different structures in large quantities. Synthetic polymers are, however, usually hydrophobic, and cells prefer to attach to polar or charged surfaces. Therefore, surface treatment of the polymer by radiation or coating by hydrophilic compounds or nano coatings has been used in different context.

Coating of surfaces with "feeder cells" are terms used to describe cells of one type that are co-cultured with cells of another type, to provide an environment in which the cells of the second type can be grown in suspension, or to provide a surface on which the cells of the second type can be grown semi-adhered. The feeder cells are optionally from a different species as the cells they are supporting. Feeder cells may be one of the fibroblast types or the extra-cellular matrices such as Matrigel and laminin.

Coating of fibre surfaces does have other purposes like anchoring the fibres to each other in order to increase stiffness, mechanical strength of the permeable body. Such a binder in solutions could be resins, epoxy, melamine, polyvinyl alcohol, polyvinyl acetate or the like. Surface coating may also be impregnation with absorbent powders such as activated carbon, pyrolytic carbon, diatomaceous earth, perlite cay or such. Similar or other materials, molecules or proteins embedded in the matrix material carrying a positive (cationic) electro kinetic charge and chemically bonded to the matrix will further improve also the mechanical strength. Since most micro organism and contaminants found in the media are negatively charged (anionic), they will be inherently attracted to the charged matrix.

Media Composition

Today, there is a multitude of different nutrient compositions for specific cell or micro organism types. Basically they are all based on:

Carbon source and/or energy source
Organic nitrogen source
Minerals
Vitamins

Glucose concentration should not fall below 1.0-1.5 g/L with initial glucose concentration of 1-5 g/L) though highly depending on the micro organism cultivated. $CO_2$ concentration is an important factor for adjusting the pH level with ratio to $O_2$~1:5 and tension of $CO_2$ ranging 1-10%.

Oxygen Supply Considerations

In an aerobic process, optimal oxygen transfer is perhaps the most difficult task to accomplish. Oxygen is poorly soluble in water, even less in cultivation or bio-reactors. Oxygen content in the nutrient is highly important and cells like CHO constantly need 0.31 pmol/cell/h. As Oxygen is poorly dissolved in water $O^2$ access often becomes the limiting factor for cell growth and protein expression. Oxygen transfer is usually helped by sparging (gas bubble flushing) and agitation, which is also needed to mix nutrients and to keep the cultivation homogeneous in stirred tanks. There are, however, limits to the speed of agitation, due both to high power consumption (which is proportional to the cube of the speed of the electric motor) and to the damage to the micro organisms caused by excessive impellor tip speed in traditional suspension vessels or bags.

One feature of the present invention is the compactness, which allows the matrix to be included permanently within a single-use container also including a micro bubble sparging (oxygenator) unit. And by controlling the media flow and direction including the bubbles its possible to separate bubble to micro organism contact by introduction of membranes within the vessel. Such separation membrane with selected porosity acts as a barrier to the bubbles, allowing media to pass un-restricted keeping bubbles on the opposite side of the bioreactor. The principle FIGS. 12 and 13 also allow a set-up, where the impeller of pump (125*b*, 135*b*) is included within a container mutually with the oxygenator (127, 137), detailed described in example 4.

Another attractive method is the use of the "oxygenator", which is a medical device capable of exchanging oxygen and carbon dioxide in the blood of human patient in surgical procedures that may necessitate the interruption or cessation of blood flow in the body, a critical organ or great blood vessel. It's a disposable device and contains about 2-4 $m^2$ of a membrane permeable to gas but impermeable to fluids, in the form of hollow fibre module. Pore size in such hollow fibres range 1-200 nm though operating at several Bars of pressure. Combined in the bio-reactor external fluid circuit (FIG. 12 and FIG. 13), the oxygenator is most likely located outside the bio reactor as a separate reactor to which the nutrient pass through before being entered to the bio reactor. The oxygenator sees on the other side of the membrane either air, oxygen or a controlled gas composition in order to control the dissolved gases in the media.

Seeding Considerations

Nutrient velocity dynamics and flow profile though the matrix have huge impact on the spontaneous deposits of the micro organism prior to colonization of the matrix. Relative strength of adhesion are related to initial surface tension of the matrix surface and reflects the integrity of the first conditioning films, which is usually dominated by proteins. Fluid flow effects, such as shear stresses also play a critical role in the process of inoculation. For semi-adherent and suspension cells the dynamics are somewhat different as the fluid flow forces play an important role for where in the porous structure the micro organisms agglomerate and start to colonise the matrix.

Expression Considerations

Current expression rates by mammalian cells depend upon the type of molecule to be expressed and the basic rule is that high surface area enables high cell yields for adherent cells. For suspension cell lines in general present day technologies are faced with the fact that cell density drop from $2\text{-}5 \times 10^{*7}$ cell/mL on the best 500 mL bench-top bio-reactors with a factor 10-100 to maximum industrial volume stirred tank.

Based on common available reference the following general data for is obtained from relevant available commercial data, advertising, articles:

Bench-top batch operation in very small scale on adherent CHO cells:

The BelloCell/FibraStage 500 mL volume bottles can offer cell density of $2 \times 10^{*8}$ cells/mL.

T-flasks or roller bottles can offer adherent cell density of $1\times10^{*7}$ cells/mL. Replace media regularly.

Bench-top batch mode operation on CHO adherent cells in 1-15 liter volume:

The CelliGen with 50 gram FibreCell fibre discs can offer cell density of $1\times10^{*8}$ cells/mL.

The FiberCell hollow fibre can offer cell density of $1\times10^{*10}$ cells/mL.

OptiCell ceramic carrier, perfusion mode, could offer cell density of $1\text{-}2\times10^{*6}$ cells/mL.

Replace media regularly.

Pilot scale batch operation 15-100l volume on CHO suspension cells:

Fluidised bed with micro carriers can offer adherent cell density of $1\times10^{*8}$ cells/mL.

Stirred tank suspension system can offer cell density of $5\times10^{*7}$ cells/mL.

Wave bag suspension system can offer cell density of $1\text{-}10\times10^{*6}$ cells/mL.

Industrial scale operating 100-250 liter volume on CHO cells:

Fluidised bed with micro carriers can offer adherent cell density of $1\times10^{*7}$ cells/mL.

Stirred tank can offer suspension cell density of $5\text{-}10\times10^{*6}$ cells/mL.

Perfusion system can offer cell density of $1.5\times10^{*8\text{-}6}$ cells/mL.

Production values, data was somewhat more difficult to obtain:

T-flask, less than half liter medium, $2\times10^{*9}$/mL cells, express 1.5 mg/L/day Bench-top-Celline CL1000, stirred, suspension, $1\times10^{*7}$ cells/mL, express 25-50 mg/L/day Pilot scale—Wave bag produce 10-50 mg/L/day Pilot scale—stirred, batch, $1\times10^{*7}$/mL cells, express up to 200 mg/L/day Bench-top—CelliGen, FibraCell fibre discs, 1 liter volume, express up to 500 mg/L/day Productivity/titer per liter reactor volume, CHO cells for antibody production.

Alternatively its possible to express the volumetric productivity in picograms per cell per day. In 1986 the industry standard was 10 pg/cell/day for CHO cells. By 2006 the absolute highest product titer has ten fold increased to 100 pg/cell/day equivalent to 500-1,000 mg/l/day. Though its more realistic to expect 20-60 pg/cell/day expression capacity for CHO cells. All off the above are not achieved by increasing cell density, but entirely by optimised cell performance through better nutrient and conditions. Even with cell culture density of $1\times10^{*7}$/mL cells the total biomass represent less than 5% of the culture volume and leaves plenty room for the here presented invention.

Multiplication Considerations

The stem cells advantageously used according to the invention are human stem cells chosen from the group consisting of embryonic stein cells at the origin of somatic stem cells, and/or stem cells/somatic progenitors themselves at the origin of blood and/or various solid tissues such as the skin, the liver, the pancreas, the heart, the kidney, bone or nerve tissue. Most types of stem cells multiply preferably as immobilized cells adhered to "feeder cells" for symmetrical proliferation. Feeder cells are terms used to describe cells of a second type (also mammalian or human) that are co-cultured with cells of another first type (such as stem cells). The invented bioreactor permeable body provides an attractive environment in which the cells of the second type can be grown in suspension or adhered to or semi-adhered to the permeable body surfaces. Hereby providing an attractive surface on which the cells of the first type can be grown semi-adhered to or agglomerated on. The feeder cells supply the stem cells with the required nutrient. The second important feeder cells are optionally from a different species as the first important cells they are supporting for multiplication purposes. Feeder cells may further be of the fibroblast types or the extra-cellular matrices Matrigel and laminin.

EXAMPLES

Example 1

Documented Performance

Reference is made to the work of Guozheng Wang, et. al documented in the article "Modified GelliGen packed bed bio-reactor for hybridoma cell cultures" Cytotechnology 9, page 41-49, 1992. Two test were performed on the New Brunswick Scientific product named CelliGen 2.5 liter reactor.

1. a packed-bed column system packed with 50 gram FibraCel carriers (500 mL volume) in perfusion mode with 200 mL/min external pump controlled nutrient flow and $\sim 1\times10^{*8}$/mL cells with expression of 0.5 g/L/day MAbs.
2. a packed-bed basket system packed with 110 gram FibraCel carriers (1,000 mL volume) with 3,000 mL/day nutrient flow with internal perfusion circulation pump and $\sim 1\times10^{*8}$/mL cells with expression of 0.5 gram/L/day MAbs.

Examples 2

Polyester Fibre Discs

For the present invention, in a mass production scale, in a disc stacked body the nutrients, fresh media to the CHO micro organisms is introduced internally and pumped through the reactor constantly to the circumference drainage of the reactor. FIG. 1 illustrates how the discs are oriented with central feed inlet and circumference drainage outlet for even mass flow though each cm³ of the sheets. As the fibre based discs is able to support $1\times10^{*8}$/mL CHO cells, then:

In a 70 liter container the present invention offer $4\times10^{*4}$ cm³ of porous matrix volume in the stacked sheets based on non-woven fibre felt sheets Documentation from individual sources show that conservatively $1\times10^{*8}$/mL CHO cells are able to produce 500 mg/L/day proteins, when anchored on randomly oriented polyester fibre bodies (FibreCell)

In 1 cm³ porous substrate of this invention the cells then under best conditions express 500 mg/mL/day protein Multiplying the volume and production rate gives this excellent figure of 40 liter×500 mg/L/day=20 gram/day Example 3

Non-woven Matrix

A fermenter assembly and method as depicted in FIG. 12 was tested at Aarhus University in Denmark with HEK293 cell line. The reactor as seen in FIG. 12 of which (121a) consisted of a six single envelope compartment in which non-woven polyester matrix sheets supplied by company Fibertex in Denmark. The envelope diameter was 80 millimeter and the total volume of the matrix (121) was approximately 610 cm³ and the medium volume 1908 cm³. An external media loop with a flow rate of 100 mL/min drew from the bottom of the reactor through an oxygenator (hollow fiber module UFP-3-C-4A, GE Healthcare) and a pump before medium entered the centre of the matrix module again. The oxygenator (127) on the permeate side had a steady flow of 95% air/5% $CO_2$ to supply oxygen and control pH. The reactor dO, pH, temperature data were collected, harvest and feeding controlled with a BioStatB DCU unit (Sartorius) and custom-made data acquisition software (Foxylogic.com).

To reduce the hydrophobicity and to increase the biocompatibility, the non-woven PET matrix discs were rinsed twice with 95% EtOH for 2 hours and then treated with 1% w/v NaOH for 1 hour at ~100° C., followed by extensive rinsing with water. The matrix discs were then packed into the fermenter (4 disc pieces per stack in total 18 millimeter thick per stack; total of 6 stacks with flow-net spacers in-between similar to FIG. 1) and the reactor assembly rinsed with PBS-buffer. The reactor was equipped with dO (dissolved Oxygen), pH and temperature probes, external loop and oxygenator was then autoclaved. Following, the reactor was treated with 40 mL sterile PBS-buffer with 200 Units/mL Penicillin-Streptomycin with 5 mg poly-L-lysine to increase the biocompatibility, enough to fully wet the matrix. The mixture was left to rest for 5 min, and then supplemented with 750 mL PBS-buffer with 200 Units/mL Penicillin-Streptomycin. Buffers were pumped into the fermenter via the feed using the pumps on the BioStat-B DCU unit. The circulation pump was started and left for 30 min to rinse tubes and reactor. Air trapped in the matrix stack was driven out through (126). The bio-reactor was then drained via both the feed and harvest lines using the pumps on the BioStat-B DCU unit, and rinsed with 500 mL sterile PBS-buffer with 200 Units/mL Penicillin-Streptomycin followed by a rinse with 500 mL DMEM medium with Glutamine, 100 Units/mL P/S) and 10% serum was pumped into the fermenter via the feed line (125*c*) and circulated for 10 min, then drained. The matrix retained volume was measured to ~50 mL. Finally, the fermenter was filled with DMEM medium. The temperature stabilized at 37° C. after 1.5 hours. The dO probe was allowed to repolarise for 8 hours, then left for 2 hours without air supply to check that no infection was present.

The fermenter was seeded with 130 mL of seed culture of HEK293 cell line with a total of $4 \times 10^8$ cells, viability >95%, were added to the fermenter through the seed line with a flow of 6 mL/min. The reactor flow was set to a flow of 200 mL/min (0.8 cm/min flux) for 1 hour to allow cells to move into the matrix before the reactor was left for the rest of the 7 day experiment with at flow of 1,000 mL/min (4 cm/min flux). Seed density in the non-woven polyester matrix was calculated to ~$1.8 \times 10^6$ cells/mL matrix volume. Final cell density after experiment was measured to be $7 \times 10^7$ cells/ml matrix. For the following days the reactor was monitored for cell activity by tracking glucose consumption and antibody production. Glucose consumption was monitored using an enzymatic D-glucose kit (R-Biopharm GmbH) and antibody titer measured using capture on a Protein-G HP column on a HPLC system. Medium exchange was started at day 3 at a rate of 0.5 reactor volume/day (with DMEM medium) increased to 6 reactor volume/day at experiment end.

Example 4

Matrix and Container Combination

The principle FIGS. 12 and 13 also allow a set-up, where the impeller of pump (125*b*, 135*b*) is included within a container mutually with the oxygenator (127, 137). Such an example of design has been created by company CerCell® in Denmark combining CellCore, being the present invention, with the CellReady 3 liter stirred tank bioreactor manufactured by Millipore® in the US. The CellReady is a single-use 3 liter cast rigid plastic container including a traditional triple blade propeller mounted on a shaft for suspension cultivation purposes only. CerCell replaced the CellReady impeller with a custom designed centrifugal impeller, integrated with the CellCore reactor body, for media re-circulation purposes internally within the CellReady vessel. Items (121, 131) and (125*b*, 135*b*) and (127, 137) are all mounted internally, inside the CellReady using the CellReady container as the re-circulation line (122, 124) and (132, 134). The pump (125*b*, 135*b*) is operating inside the CellReady container and the drive motor is mounted outside on the top of the CellReady top cover. A shaft connects the top mounted drive motor with the pump.

Matrix volume calculated to be 595 cm³ with a media feed surface area of 330 cm². The pump was able to re-circulate one liter of media per minute via line (122, 124, 132, 134) equivalent to a flux of 3-8 cm/min. Dissolved Oxygen was measured to 60% with 50 kPa $O_2$ pressure on the integrated oxygenator, sparging unit (127, 137) with in this example a sparging unit surface area of 2 cm².

The described set-up allows significant increased micro organisms densities in suspension as well as semi adherent micro organisms. Other similar set-up is obvious in other bio containers from other brands.

Items of the Present Invention

The following section discloses aspects and embodiments of the present invention present in the form of items as cited herein below.

1. A bio-reactor apparatus for culturing stem cells, living cells or mobilized micro organisms, comprising a porous three-dimensional matrix, said matrix surrounded by porous walls arranged in parallel or partly in parallel with a bio-reactor inlet separated from a bio-reactor outlet by said porous walls, wherein said bio-reactor inlet is capable of diverting feeding liquid to the matrix in a flow path having a first orientation, wherein said core, via hydronic forces, conveys fluids to pass each of the individual core matrix parts perpendicularly to said first orientation, wherein said matrix is suitable for anchoring and/or supporting the growth of living cells.

2. A modulus build bio-reactor device prepared according to item 1, where the individual porous bodie(s) of the core are fibre based sheets assembled around an inlet volume forming liquid distribution passages with an exhaust volume for liquid distribution passages and further arranged in such a way that the inlet volume are separated from the outlet volume by the sheets of porous material hereby creating a parallel structure.

3. A modulus build bio-reactor device prepared according to any of the previous items, wherein the core is assembled from discs structures suitable for stacking said discs being shaped to desired configuration such as round, square, rectangular or combinations hereof comprising an liquid distribution passage inlet volume with an exhaust liquid distribution passage volume and further arranged in such a way that the inlet volume are separated from the outlet volume by the sheets of porous material. The discs further stacked in such a way that said discs are assembled two-by-two creating a symmetrical arrangement with inlet volume in between each inlet set of discs corresponding with the common inlet and the outlet volume are isolated from the internal volume by the three-dimensional porous matrix which on the outlet side of the discs corresponding with a common outlet at the circumference.

4. A modulus build bio-reactor device prepared according to any of the previous items, where the porous matrix core are non-woven or woven fibre based sheets arranged pleated or stacked with inlet annular liquid distribution passages around a cylindrical inlet volume with an exhaust volume external to and surround the annular liquid distribution passages of the core and further arranged in such a way that the inlet volume are separated from the outlet volume by the sheets of porous material and the closed core ends hereby creating a parallel structure. Further being a plurality of longitudinal pleats, each of the pleats having a pair of legs, each of the legs having a first and a second surface, the pleats being in a laid-over state in which the first surface of one leg of one pleat is in intimate contact with the first surface of an adjoining leg of said one pleat and the second surface of said one leg is in intimate contact with the second surface of an adjoining leg of an adjacent pleat over substantially the entire height of each leg and over a continuous region extending for at least approximately 50% of the axial length of the bio-reactor device.

5. A bio-reactor device according to any of the previous items, wherein the configuration is of spiral design being circular assembling a number of matrix core envelopes sandwiches around drainage spaces and separated by feed spacers.

6. A modulus build bio-reactor device prepared according to any of the previous items, where the enclosure for porous bodies, grain, micro spheres or fibres are shaped by at least one stackable envelope of porous materials around a central inlet device, a circumference outlet hereby creating a radial channel system and ultra compact parallel structure such envelope material having porous walls.

7. A modulus build bio-reactor device prepared according to any of the previous items, where the individual porous body(s) of the core is a based on a porous organic foam matrix.

8. A bio-reactor device prepared according to any of the previous items, wherein the support is a honeycomb structure with a first plurality of blind separation cavities extending perpendicular into said body from said inlet side surface and a second plurality of blind separation cavities extending perpendicularly into said body from said outlet side surface, said blind separation cavities of said first and second pluralities being arranged spaced apart and mutually juxtaposed, the membrane bio-reactor device being composed of a number of longitudinal porous membrane bio-reactor device elements assembled so as to form said separation cavities, the method comprising transmitting the liquid into the first plurality of blind separation cavities and perpendicular through the porous walls into the second plurality of blind separation cavities.

9. A bio-reactor device prepared according to any of the previous items, wherein the support is a honeycomb structure with sets of circular blind separation cavities extending perpendicular into said body from said inlet side surface and a second set of plurality of blind circular separation cavities extending perpendicularly into said body from said outlet side surface.

10. A bio-reactor device according to any of the previous items comprising:
   a) a membrane supporting three-dimensional porous matrix structure
   b) a porous membrane on the outlet, down stream side of the membrane supporting structure, said supporting structure having a nutrient inlet face, a membrane outlet face and a thickness or porous matrix in between said faces, said bio-reactor having in operation a biolayer on the three-dimensional porous wall matrix surfaces between the nutrient inlet and the outlet membrane; wherein the matrix allows diffusion of a nutrient solution from the nutrient face to sustain, feed the biolayer or micro organism allowing the biolayer product to pass through the porous matrix and the fine pored membrane(s).

11. A modulus build bio-reactor device prepared according to any of the previous items, wherein the core is a discs structure suitable for stacking and hereby creating a parallel structure. The stacked discs being shaped, cast, moulded to desired configuration. Said discs stacked in such a way that the discs are assembled two-by-two creating a symmetrical arrangement so the inlet space in between the disc corresponding with the common inlet for liquid distribution and the outlet are isolated from the internal volume with a membrane on the outlet side of the discs corresponding with a common outlet volume with liquid distribution passages at the circumference.

12. A bio-reactor device according to any of the previous items, where the reactor core is housed, enclosed in a container having:
   a) at least one inlet channel, hose, tube or flange for admitting the nutrient solution to the nutrient inlet face of the core structure and the nutrient re-circulation
   b) at least one outlet channel, hose, tube or flange for removing the product and the used nutrient solution from the three-dimensional porous matrix.
   or any combinations of the above.

13. A bio-reactor device or parts of a bio-reactor device prepared according to any one of the items, wherein parts of the device are based on:
   a) Synthetic polymers in general, such as; resins, polycarbonate, polypropylene, polyethylene, polyethersulfone, polyester, polyoxyethylene, polyacrylonitrile, Polysulfone, ethylene vinyl acetate, polyvinyl acetate, cellulose acetate, polytetrafluoroethylene, aramide, Polychlorotrifluoroethylene, Polyfluoroethylenepropylene, polyvinylidene fluoride, polyvinylidene chloride, polystyrene, Polyamides, acetal, acrylics and further thermoplastics in general
   b) Synthetic elastomers, rubber in general, such as silicone, ethylene propylene rubber (EPM), ethylene propylene diene rubber (EPDM), Fluoroelastomers (Viton), neoprene, polyurethane, nitrile, butyl,
   c) Natural polymers (also bio polymers) in general, any form of fibres or particles, such as; rubber, latex, cellulose, cellulose variations, dextran, chitin, collagen, fibrin, keratin, starch, paper, cotton, wool, flax, hemp, coconut, jute, resins, viscose rayon, human and animal organic structures such as bone, tissue and further carbon and carbon element containing structures in general
   d) Synthetic bio degradable polymers (bio plastics) in general, like; polyester, aliphatic polyester such as polylactic acid polymers and polyhydroxyalkanoates families, polybutylene succinate, polycaprolactone, PCL, etc
   e) Ceramics based on powders, grains and/or fibres, such as non-oxides and/or oxides and/or nitrides based on, SiC, Titanium, Aluminium, Silicon, Zirconium and their combinations
   f) Human or animal bone or skeleton substitutes such as hydroxylapatite and/or calcium phosphate and/or carbonated calcium variants g) Insects skeleton materials like chitin
h) Natural organic protein containing materials such as gollagen, gelatin and similar substances
i) Synthetic carbon fibre based substances
j) Metal powders and/or metal fibres and their combinations
k) Glass spheres, glass fibres, fibre glass
l) A binder being a glassy phases a resins or their combinations
m) Micro or macro carriers, macro beads, rasching bodies and polyester fibre porous discs less than 10 millimeter in diameter or porous micro carriers less than 5 millimeter in diameter or any combination hereof, like in any symmetric or asymmetric configuration, or any combination of materials in any shape combined.

14. A bio-reactor device according to any of the previous items, integrating at least one sensor, probe, transmitter collecting signals for a controlling device in order to obtain suitable conditions in the reactor core, the sensor designed such as;
   a) where the reactor core is enclosed in a container, bag, capsule, cassette integrating at least one sensor or probe for measurements of either of or all of; pH, dissolved oxygen, dissolved carbon dioxide, temperature, pressure and cell density, or
   b) where the reactor core is enclosed in a container, bag, capsule, cassette integrating at least one disposable, single-use sensor or probe for measurements of either of or all of; pH, dissolved oxygen, dissolved carbon dioxide, temperature, pressure and cell density
   or any combinations of the above.

15. A bio-reactor device according to any of the previous items, integrating a temperature conditioning device with the purpose to keep a suitable temperature in the reactor core, such as;
   a) where the reactor core is housed, enclosed in a double circumference wall container, said circumference volume between the container walls housing a heating device or circulating a heating fluid for exchange of heat.
   b) or where the reactor core is housed, enclosed in capsule, cassette housing a temperature conditioning device.
   c) or where the reactor core matrix parts is laminated with a temperature conditioning device integrated within the fluid carrying spacers.
   d) or where the reactor core is housed in a vessel, container, bag which is surrounded by a flexible heating element on the out side.
   or any combinations of the above.

16. A bio-reactor device according to any of the previous items or parts of a bio-reactor device prepared with adjustment of zeta potential to within the range of 2-7.5 pH generating a hydrophobic surface attraction, behaviour and micro organism friendly surface.

17. A bio-reactor device according to any of the previous items comprising an electrically conductive matrix or matrix supporting structure with electrical connections to the core in order to charge, change or modify the bio-reactor electrical potential for improved attraction of the biofilm, micro organism to the three-dimensional porous matrix.

18. A bio-reactor device according to any of the previous items, wherein the fibres, yarn, grains, spheres in the matrix is coated, covered with a surface treatment and/or a wash coat and/or a catalytically active coating and/or a nano particle coating obtaining a micro organism adhesion friendly surface or the opposite or combinations hereof.

19. A bio-reactor device according to any of the previous items, wherein the biofilm, surface layer of, agglomeration of micro organism comprising biological matter is selected from the group consisting of; bacteria, fungi, algae, plankton, animal cells, mammalian cells, tissue cells, yeast cells, plant cells, insect cells, protozoa cells, prokaryotic cells, eukaryotic cells, archaea cells or other biological matter.

20. A bio-reactor device according to any of the previous items, wherein the biofilm, surface layer of micro organism, agglomeration of micro organism express biological matter, such as; micro organism, cells, proteins, recombinant antibodies, enzymes, monoclonal antibodies, therapeutic antibodies or other biological matter.

21. A bio-reactor device according to any of the previous items, wherein the micro organism, agglomeration of micro organism multiply biological matter, such as; micro organism, cells, stem cells or other biological matter.

22. A bio-reactor device according to any of the previous items having inlet channels for admitting the nutrient solution to the nutrient inlet face of the supporting structure, and outlet channels for removal of the used nutrient solution from the three-dimensional porous matrix of the supporting structure, and an external system for replacing the used nutrient solution with fresh.

23. A bio-reactor device according to any of the previous items incorporation a single-use pumping device for fluid transport within the bio-reactor.

24. A device with design according to any previous items suitable for separation of particles from a fluid.

25. A method for industrial micro organism cultivation according to any of the previous items in a liquid using a bio-reactor device having numerous micro organisms located inside the porous matrix prohibited from passing the porous matrix by selective pore size of porous media. At least a part of the nutrient flow volume and the product outlet volume communicate only through the porous matrix wall hereby passing the micro organism.

Description to the Drawings

FIG. 1—Illustration of one embodiment of the bio-reactor according to the present invention. A total of 20 matrix sections (11) stacked individually into a column and separated by feeding spacers (15a) and drainage spacers (15b) and contained in a bio-reactor having end wall sections (10a, 10b) and a circumferential wall section (19).

The principle of the invention incorporates a plurality of identical or differently shaped matrix sections, such as discs (11) arranged adjacent to each other and around a perforated feeding tube (10c) having a central inlet (12) and an outlet (13). The design eliminates gradients and gives an extraordinarily uniform flow distribution of nutrients through the reactor and a uniform distribution of biological cells.

The individual matrix sections (11) are stacked in sets adjacent to each other and separated on the inlet side by feeding spacers (15a) acting as radial fluid flow passage ways; the feed spacers (15a) are sealed (15c) which restrict any flow connection with the circumferential collection volume (13), thereby forcing the flow axially through the matrix sections (11). Drainage spacers (15b) on the outlet side of the stacked matrix sections (11) receive the axial feeding liquid once it has passed through the matrix (11). The drainage spacers are sealed (15d) so that feeding liquid cannot flow back into the inlet zone (12), but is instead diverted to the collection volume (13) located at the circumference of the bio-reactor. The drainage spacers (15b) are in liquid contact with radial extending outlet slots which divert feeding liquid from the exit side of the matrix sections (11) to the collection volume (13)—thereby guiding the feeding liquid and bioactive compounds produced to a top collection volume (16), thereby passing a set of stacked, flow net rings (17). The symmetrical arrangement ensures that the inlet (12) and the outlet (13) are isolated from each other by the matrix sections (11)—which matrix sections represent the only flow route for the feeding liquid through the bio-reactor.

The alternating feeding spacer sections and drainage spacer sections may be symmetrical and comprise or consist of different or identical layer(s) of flow net with an array of ribs arranged coaxially, thereby allowing feeding liquid and cells to pass unrestricted. Furthermore, the spacers may be of an asymmetrical design with coarser net(s) and screens laminated on each side with finer mesh flow net layers directly contacting the porous matrix sections. The finer flow net will eliminated the intrusion of fibres, particles, grains, spheres and the like from the matrix to penetrate into the spacer volume and restrict the flow of feeding liquid. The flow path through the porous matrix sections is axial for the shortest possible path way. In one embodiment, each of the 20 matrix sections holds 112 $cm^3$ in volume, the total matrix volume being 2,300 $cm^3$ in a body ranging OD140×L250 millimeter matrix (disc) section.

FIG. 2—Illustration of one embodiment of the bio-reactor according to the present invention. Stacked matrix sections (discs) are separated by cast plastic parts creating a fully housed bio-reactor (24). A partly open view with a 90 degree cut away for clarity illustrates space for a plurality of identically shaped and stacked matrix sections (21) (3 matrix sections shown, 5 matrix sections removed) arranged along and around a central tube (22)—thereby creating a cylindrical bio-reactor container.

The matrix sections (21) are surrounded by an outlet (23) arranged in the circumference of the bio-reactor as a collection area for 3 double drainage spacers (25b) and two, end-positioned, single drainage spacers (25c), one at the top and one at the bottom of the stacked matrices.

The view is for perfusion mode operation, but could be cross-flow with an extra fluid connection in the bottom cover opposite of (24a) the inlet volume (22). The rotational, symmetrical arrangement with four conical feed spacers (25a) equipped (with ribs on each side to separate symmetrical the two neighbouring discs (21) corresponds with the common central inlet (22), but not with the common outlet (23) on the circumference, which is isolated from the inlet volume (22) by the matrix sections (21). The opposite conical design has been applied to the drainage spacers (25b) located in between 6 set of matrix sections (21). The drainage spacers are flow sealed at the centre and attached to an inner tube (25d) part facing towards the inlet (22), so the media flow freely towards the common outlet at the circumference around the core connected to the collection volume reservoir (23) encapsulating the bio-reactor core from top to bottom.

Both feed spacers (25a) and drainage spacers (25b, 25c) have on the circumferential side a short cylindrical part (24c) to ensure stable dimensions around the collection volume reservoir (23) outside the bio-reactor core and potentially a temperature conditioning device (not shown) in a tight fit around the bio-reactor (24). Said collection volume reservoir (23) corresponds with horizontal cavities (26) under top cover (27) of the bio-reactor core (24) and the only inlet (24a) and primary outlet (24d), as well as secondary outlet (24b) and corresponds with external pumps, valves, etc (not shown) for fluid control and general bio-reactor operation.

The entire set-up can be manufactured from disposable materials, such as bio compatible plastics if desired and the purpose of introducing non flexible plastics as container materials is to create a single-use system easy to dispose after use. The illustrated bio-reactor has a diameter of 145 millimeters, a height of 200 millimeters and contain 8 matrix sections each 180 $cm^3$ in total 1.5 liter volume.

FIG. 3—A 180 degree cut illustration of FIG. 2 connected with two diaphragm pumps, though the pumps are illustrated only in a simplified way. The bio-reactor (34) with space for 8 matrix sections (31) integrates symmetrically at each end a membrane pump (38a, 38b). Both membrane pumps (38a, 38b) offer an individual operation method as desired to be performed, though they are fluid interconnected through the matrix centre (32) and the circumferential collection reservoir (33). Both pump membranes (38c) is controlled from electronics (not shown) in housings (34a, 34b). Membrane (38c) in housing (38a) is fully expanded and membrane (38c) in house (38b) is not expanded. Valve fixation points (38d, 38e) (valves not shown) at each end of the fluid distribution centre (32) participate in the fluid direction control. External valves (not shown) at tubes (38f) and (38g) participate in the fluid control method. External gas pressure and electrical connection is illustrated passing a relevant number of tubes (38h). The invented combination of bio-reactor and pumps/method of operation eliminate the traditional need of external peristaltic pumps and achieve a simplified operation and lowered operation costs from single-use product.

The two identical pumps and membranes (38c) housed in pumping sections (38a, 38b) can be disposable and—at production set-up—can be supplied fully integrated with the bio-reactor (34) as a pre-sterilized package of both single-use and disposable capabilities. Items 34a and 34b, which integrate both the bio-reactor and membrane controls, are re-usable units respectively not disposable.

FIG. 4—Bio-reactor cartridge assembled from at least two envelope (40) parts (four envelopes shown), based on a semi rigid porous first matrix sheet material pre-shaped to create walls which encapsulates, and create an enclosure volume (41) for the second matrix of fibres, spheres, macro beads, grains, powders or combinations hereof.

The envelope (40) hereby appears as symmetrical core module(s) with common central fluid inlet (42) and a common outlet(s) (45b) in the circumference of the stacked core modules (40). Pore size of the envelope (40) membrane (43a, 43b) material is primarily selected to keep the fibres, spheres, macro beads, grains, powders captured by the membrane (43a, 43b) inside the envelope volume (41), but allows fluids and products to pass. The two membranes (43a, 43b) are assembled at seam 43d to circular centre part 42a with holes 42b for feed fluid to pass. The two membranes (43a, 43b) have yet a seam at the circumference 43c. For improved flow distribution, feed spacers (45a) with an array of ribs (not shown) between the envelopes (40) parts, adjacent to inlet walls (43a) ads rigidity to the envelope (40). Such spacers, or flow guides, may appear as a third matrix. The envelope (40) wall (43a, 43b) material may be of (a)symmetric structure with pore size variation suitable for the various purposes. Two or more envelopes (40) are easily assembled/stacked with inlet body seals (not shown) in between each envelope (40) centre and attached, added on top of each other, into a stack inside a suitable housing or container (not shown) creating a cartridge.

Stacked in such a way that the identical envelopes (40) create a symmetrical arrangement and the envelopes (40) share the cylindrical inlet (42) volume centre. The common inlet (42) and the common outlet (45*b*) are isolated from each other by the matrix material (41) inside the envelopes (40). Depending on fluid direction the cartridge centre (42) is the inlet or the outlet corresponding with the cartridge circumference (45*b*) is respectively the outlet or the inlet. At least two of the envelopes (40) may also be stacked inside vertical oriented capsule housing with a bottom part for at least two fluid connections and a housing dome attached with a flange and seal to the bottom part flange. The capsule may have similar design as to the capsule overall design as shown in FIG. 5.

FIG. 5—A variation of the invention is for integration purposes into a column and the bio-reactor matrix core modules is fully situated inside a stackable capsule device (50) of rigid disposable materials with at least one fluid inlet (52)*a* and a series of symmetrical placed fluid outlets (52*b*) integrated axially within the capsules (50) overall design. Four radial oriented and in parallel fluid outlet ports (52*b*) are connected to drainage collection volume (53) at the capsules periphery. The bio-reactor capsule design encloses at least one set of matrix discs (51) and as here illustrated five sets of matrix discs (51). No flow spacers at the feed (52*a*) and drainage (55*b*) volumes between matrix discs (51) are shown for simplicity. Drainage spacers open to the collected volume (53) and closed by connection to a short tube (55*d*) next to the inlet volume (52). Feed spacer volume (55*a*) is not able to convey fluids to the circumference volume (53) by integrated ring (55*c*). The fluid is limited by entering from volume (52) directly to discs (51) at it edge by ring (55*d*) and also restricted from exiting the discs (51) to the collection volume (53) by ring (55*c*). The forced fluid flow is introduced at one of two inlet (52) filling up the inlet volume (52), distributed to four full size and two half size feed spacer entrance (55*a*) tangentially filling the feed space laminar at overpressure flowing perpendicular to the entire surface area of at least one matrix disc and through the disc for drainage spacer volume (55*b*) further radial into circumference collection volume (53) to be conveyed to end face collection volume (56) and outlet (52*b*). More than one bio-reactor capsule may be mounted on top of each other working in parallel and sealed by (50*a*) covering both inlet (52*a*) and exit (52*b*).

After the fluid has passed said fluid device the fluid may possible pass further to at least one manifold capsule, pump capsule, conditioning capsule as to the CerStack patent application (PCT/DK2009/000260—not shown). The illustrated capsule is 442 millimeters in diameter, 256 millimeter high, but may take other dimensions as required.

FIG. 6—A bio-reactor cartridge (flexible fibre sheet based pleated core) having a cylindrical shape with a longitudinal axis and a plurality of longitudinal pleats each separated by drainage spaces. The pleat material (62) may preferably be a porous material like at least one non-woven sheet of symmetrical or asymmetrical design in at least one layer. Each pleat is on both the inlet, upstream and the outlet, downstream separated by spacers (63*a*, 63*b*) for flow guidance. The drainage spacers (63*a*, 63*b*) may be symmetrical, identical layer(s) of at least one flow-net, screen with an array of ribs arranged coaxial allowing fluids in general and cells during feeding to pass unrestricted. Further the spacers (63*a*, 63*b*) may be of asymmetrical design with coarser flow-net laminated on each side with finer mesh flow-net layers in direct contact with the porous matrix. The finer flow-net will eliminated the intrusion of fibres, particles, grains, spheres from the matrix (62) to penetrate into the spacer volume and restrict the flow passageway. The pleated core (62) includes an upstream inlet volume for fluid distribution further include a cylindrical rigid flow-net (63*c*) in centre (64*a*) surrounded by the flexible pleated matrix core (62) said cylindrical centre correspond with longitudinal oriented feed spacers (63*a*) forming semi ridged positioned in between the pleated sheet (62) in order to maintain the space between the pleats (62). The core includes on the downstream an outlet distribution volume (64*b*) for mutual fluid collection from the individual drainage channels with spacers (63*b*) between the pleats (62), the collection volumes (63) only receives fluids which passed the core. End caps or other means is necessary in order to passively separating the inlet for outlet (not shown). The common inlet (64*a*) and the common outlet (64*b*) are isolated from each other by the matrix enclosure and end caps. Depending on fluid direction the cartridge centre (64*a*) is either the inlet or the outlet corresponding to the cartridge circumference (64*b*) is respectively the outlet or the inlet. A variation is the encapsulation of the illustrated cartridge into a capsule, cassette with external connection, which may be easily sterilized for single-use application. Said bio-reactor cartridge comprises individual and in parallel oriented matrix walls each separated by a shared feed spacer section conveying fluids for mutually diverting of the feeding liquid to both individual matrix sections on each side of the feed spacer.

FIG. 7—A bio-reactor cartridge (flexible fibre sheet based spiral core) having a cylindrical shape with a longitudinal axis and a plurality spiral oriented layers of non-woven porous sheets (72) laminated around the drainage spacer (73*b*) and with on each side the feed spacers (73*a*) all wound around a central perforated fluid collection pipe (73*c*) in the core (74). The drainage spacer (73*b*) is shorter and less wide than the matrix sheet (72) and on three sides sealed from the feed stream with seals (72*a*) between the matrix sheet (72), the drainage spacer (73*b*) is connected to the collection tube (73*c*) for fluid connection, which hereby form an envelope around the drainage spacer (73*b*), which is open to, connected to and in unhindered fluid correspondence with the fluid collection tube (73*c*). The feed spacers (73*a*) are open on all four sides to the feed flow, and with no fluid connection to the fluid collection tube (73*c*) except through the matrix sheets. Said cartridge comprises individual and in parallel oriented matrix sections each separated by a feed spacer section for mutually diverting feeding liquid to both individual matrix sections on each side of the feed spacer.

FIG. 8—The illustration show a body (81) with identical wall thickness all through the embodiment and two sets of opposite direction oriented conical channels (82, 83) each channel closed in only one end opposite to the inlet opening. One set of channels being the inlet channels (82) which are closed (87) in the opposite end to the fluid inlet further the drainage channels (83) of identical dimension, but of opposite arrangement. The design creates the Wall-Flow-Filter with the purpose to force fluids evenly through the walls macro porous matrix (84). The fluid flow being laminar up through the feed channels (82) and perpendicular to the porous matrix walls 84 as to the fact that the channels are conical.

FIG. 9—The illustration show an embodiment like FIG. 8 (with even wall thickness) with conical channels and flanged to be incorporated inside a housing (not shown) around the flange with fluid connections and flow direction from down and up. The fluid interring the matrix core (91) bottom inlet face to every feed channel (92) pass along the entire channels length, but are restricted from passing through the small end of the channel of the core (91) as the feed channel (92) is closed with blockage, plugs (97) in the end opposite of inlet face (95) conveying the fluid only along the inlet channels (92) and perpendicular through the porous wall (94) of the core (91) to the four drainage channels (93) around each feed channel (92). The figure show an axial cut through the centre of a "dead-end" honeycomb structure with the porous walls (94) arranged next to each other extending from one end to the other. A plurality of blind end channels (92, 93) extends each lengthwise from one end of the body to the other end with even wall thickness to form a wall-forced-flow body. Like a chess board every feed channel is closed in one end and every drainage channel in the other end. The core (91) is illustrated with a micro pore membrane (98) with pores finer than the macro pore matrix (91), the membrane placed on the drainage channels surface of the core for restriction purposes, inclusion, separation of desired particles and micro organism in the core matrix (91). Alternatively the feed channels are of different size and larger than the drainage channels being smaller in cross section. Design and functionality is suitable both as bio-reactor and separation devices.

FIG. 10—This embodiment is based on a rigid body (101) with non parallel walls and channels rotation symmetrical around the centre axis. Preferably cast, vacuum cast or pressed with conical feed channels (102) and conical drainage channels (103) separated by quite thick macro porous matrix walls (104) here being app 15 millimeter thick or 1.2 times thicker than the feed channel (102) inlet. The conical shape of the feed channel (102) as well as the shape of the drainage channel (103) insures laminar flow along the circular channel/even fluid speed over the channel cross section from the inlet face (105) up through every feed channel (102), which all are blocked (107) at the outlet face (106) opposite of the inlet face (105) hereby forcing an even mass flow perpendicular through the entire core (101) porous wall matrix (104) to every drainage channel (103) and to the core outlet face (106). Channel blockage (107) width is identical at both inlet face (105) and outlet face (106). The blockage end (107) wall inside width is 2.3 times smaller than the feed channel (102) inlet widths. The body may take other dimensions in order to suit specific tasks like the purpose of acting as a bio-reactor or a separation device. The illustrated embodiment measure over the flange OD282 millimeter, 144 millimeter high, total volume (matrix+channels) of 7,400 $cm^3$, matrix volume of 4,550 $cm^3$ and the matrix is them 61% of total volume, but may take other dimensions as required.

FIG. 11—The core matrix (111) is as an alternative design to FIG. 10 illustrated with a micro porous membrane (118) with pores finer than the core (111) mounted on the outlet side of the core channel surface (113) for separation, restriction purposes like inclusion of desired particles, micro organism within the core matrix (114). Fluid passes the core (111) similar to FIG. 10. The macro porous body may take other dimensions in order to suit specific tasks like the purpose of acting as a bio-reactor or a separation device.

FIG. 12—Method—A production bio-reactor devise (121) incorporated inside a container (121*a*) with fluid connections situated in a re-circulation fluid circuit driven continuously by at least one controlled pump. The bio-reactor (121) is operated in a perfusion system configuration with one inlet (122) and two parallel outlets (123, 124) also appearing as a part of the loop. A pump (125*b*) controls the circuit re-circulation flow. The pump (125*c*) controls the inlet feed of fresh nutrient and somewhat the system pressure. An air trap (126) mounted at the highest point insures bubbles are removed constantly if needed. Sensors measure the glucose, pH, temp, oxygen content, etc. and regulate the flows, valves accordingly. Further the system working pressure and the $CO^2$ content inside the reactor are measured. The oxygenator (127) insures via both way diffusion through the hollow fibre membranes (or as bubble from a sparging unit) the desired $O^2$ supply and $CO^2$ removal/stripping in the nutrient flow. Ratio between $O^2$ and $CO^2$ has huge influence on the pH value and the gas supplies is regulated independently and supplied to the circuit via valve (129). The pump (125*c*) introduces the nutrient fluid to the circuit continuously from the external nutrient feed supply and at the same time the PC/PLC controls the fluid volume exiting (123) the circuit to the product vessel for external processing via the pump (125*a*). The pump (125*b*) maintains the flow and circulates the perfusion volume through the reactor (121). Sensors measure the glucose and oxygen content and a PC/PLC regulate the relevant gas injection accordingly through valve (129).

FIG. 13—Method—A production bio-reactor devise (131) incorporated inside a housing (131*a*) with fluid connections situated in a re-circulation mode with at least one fluid circuit driven continuously by at least one pump. Within this method the bio-reactor (131) housing is equipped with one reactor liquid inlet (132) and two separated reactor liquid outlets (133, 134) where (134) also appear as a part of the media loop, performing the cross-flow mode principle. The inlet flow volume through inlet tube (132) to the reactor is the combined permeate flow through outlet (133) and the retentate flow through (134). The retentate flow (134) outlet is externally re-circulated by feed pump (135*b*) and kept preferably at constant pressure controlled by pump (135*c*) and (135*a*) combined. The bio-reactor (131) product flow exit (133), which is not included in the separate permeate volume flow (134), is regulated by a positive displacement pump (135*a*) in order to obtain the desired flow over the bio-reactor matrix (131) eliminating the matrix (131) gradient by constant removal of permeate and lactate, etc. Environment regulating gases is supplied via and controlled by valve (139). Supply of dissolved oxygen is injected to the media in oxygenator (137) (or injected to a sparging unit) via external $O^2$ supply (not shown). A third pump (135*c*) controls the inlet feed of fresh nutrient to compensate for the permeate flow losses. An air trap (136) mounted at the highest point insures potential trapped air is removed constantly. The oxygen pressure supplied to the oxygenator (137) regulates the dissolved oxygen in the nutrient feed flow.

Although some figures show cylindrical inlet volume such may be conical in order to obtain laminar flow behaviour and the circumference of the invented bio-reactor may also take other shapes as being cylindrical.

Some of the capsule, cassette examples are shown with central inlet and circumference outlet. This flow pattern is in no limiting and may be reversed according to the application. Feed and drainage may further be designed to take place in the centre and a ring area around the centre for internal capsule fluid correspondence also eliminating the circumference as drainage collection area.

While the present invention has been described in connection with particular embodiments thereof, it will be understood by those skilled in the art that many changes and modifications may be made without departing from the scope of the invention as defined by the appending claims.

I claim:

1. A bio-reactor for culturing micro organisms in suspension,
   wherein said bio-reactor has
   a) a volume comprising a member selected from the group consisting of an envelope, a matrix, a scaffolding, a porous body and/or a packed bed of growth bodies for hosting micro organisms in suspension, and
   b) one or more bio-reactor inlet port(s) and one or more bio-reactor outlet port(s),
      wherein said envelope, matrix, scaffolding, porous body and/or packed bed of growth bodies is suitable for supporting the cultivation of micro organisms in suspension and expression of biologic compounds,
      wherein said envelope, matrix, scaffolding, porous body and/or packed bed of growth bodies separates said one or more bio-reactor inlet port(s) from said one or more bio-reactor outlet port(s),
      wherein the envelope, matrix, scaffolding, porous body and/or packed bed of growth bodies is in direct contact with one feeding spacer section and one drainage spacer section, respectively, on opposite sides of the matrix, scaffolding, porous body and/or packed bed of growth bodies,
      wherein the feeding spacer section and drainage spacer section is a member selected from the group consisting of a layer of flow-nets, screens, corrugated sheets, nettings or rib stiffeners, set of ribs or discs with a radial set of ribs or combinations thereof and
      wherein a gradient free laminar flow is created in the volume comprising a member selected from the group consisting of an envelope, a matrix, a scaffolding, a porous body and/or a packed bed of growth bodies when fluid is introduced into the bio-reactor inlet port.

2. The bioreactor of claim 1 wherein the envelope, matrix, scaffolding, porous body and/or the packed bed of growth bodies is selected from discs or envelopes.

3. The bioreactor of claim 1, wherein one or more of the envelope, matrix, scaffolding, porous body and/or the packed bed of growth bodies are alternately separated by feeding spacer sections and drainage spacer sections, respectively, so that each feeding spacer section provides feeding liquid, media to each of a first set of two adjacently located, envelope, matrix, scaffolding, porous body and/or the packed bed of growth bodies and so that each drainage spacer section receives feeding fluid, media from each of a second set of two, adjacently located, envelope, matrix, scaffolding, porous body and/or the packed bed of growth bodies.

4. The bioreactor of claim 1, wherein essentially all feeding liquid media entering the envelope, matrix, scaffolding, porous body and/or the packed bed of growth bodies from the side of the envelope, matrix, scaffolding, porous body and/or the packed bed of growth bodies on which the feeding spacer section is located is diverted through the envelope, matrix, scaffolding, the porous body and/or the packed bed of growth bodies and exits the envelope, matrix, scaffolding, porous body and/or the packed bed of growth bodies on the opposite side of the envelope, matrix, scaffolding, the porous body and/or the packed bed of growth bodies, where the drainage spacer section is located.

5. The bioreactor of claim 1, wherein a first set of two adjacently located, envelope, matrix, scaffolding, porous body and/or the packed bed of growth bodies and a second set of two adjacently located, envelope, matrix, scaffolding, porous body and/or the packed bed of growth bodies have one body in common where the feeding spacer section and the drainage spacer section are positioned next to each other in the bio-reactor and are contacting opposite arranged surfaces of one and the same envelope, matrix, scaffolding, porous body and/or the packed bed of growth bodies.

6. The bioreactor of claim 1, wherein the overall flow of feeding liquid media through each envelope, matrix, scaffolding, the porous body and/or the packed bed of growth bodies is essentially in a direction which is perpendicular to the direction of the flow of feeding liquid media along the feeding spacer section feeding said envelope, matrix, scaffolding, porous body and/or the packed bed of growth bodies, so that the porous matrix of the envelope, matrix, scaffolding, porous body and/or the packed bed of growth bodies exerts a "cross-flow" effect on the feeding liquid media.

7. The bioreactor of claim 1, wherein once feeding liquid media exits the envelope, matrix, scaffolding, porous body and/or the packed bed of growth bodies it is diverted along the drainage spacer section in a direction which is also essentially perpendicular to the direction of flow of feeding liquid through the envelope, matrix, scaffolding, porous body and/or the packed bed of growth bodies.

8. The bioreactor of claim 1, wherein the pores of the porous matrix of the envelope, matrix, scaffolding, porous body and/or the packed bed of growth bodies are larger in diameter than the micro organisms to be hosted and cultivated, thereby allowing said micro organisms to reside in said pores during all or part of the duration of the cultivation process.

9. The bioreactor of claim 1, wherein the bio-reactor is fitted with or connected with a liquid media pump in order to ensure the desirable flow rate is obtained.

10. The bioreactor of claim 1, wherein the bio-reactor is further fitted with sensors and transmitters for measuring, such as optical and / or single-use connected to a control unit for controlling the conditions of hosting and culturing of the micro organisms and measuring the operation conditions, such as temperature, pH, and/or glucose concentration, and/or lactate concentration, oxygen concentration and/or carbon dioxide concentration.

11. The bioreactor of claim 1, wherein the thickness of the porous matrix of said envelope, matrix, scaffolding, porous body and/or the packed bed of growth bodies, is preferably less than 500 millimeters and preferably more than 0.1 millimeter.

12. The bioreactor of claim 2, wherein the diameter of the discs is preferably less than 1,000 centimeters, such as less than 500 centimeters and preferably more than 1 centimeter.

13. The apparatus of bioreactor of claim 1, wherein the porous matrix is made of a material having bulk density preferably in the range of from 10 to 5,000 gram/dm$^3$, such as from 100 to 5,000 gram/dm$^3$, and a porosity lower than 99%, such as lower than 98%.

14. The bioreactor of claim 1, wherein the number of envelopes, matrices, scaffoldings, porous bodies and/or the packed bed of growth bodies is in the range of from 2 to 100.

15. The bioreactor of claim 1, wherein the porous matrix constitutes a non-woven material, a non-woven fabric, a woven fabric, a spun fabric or knitted fabric.

16. The bioreactor of claim 1, wherein the porous matrix is based on growth bodies made of a material selected from the group consisting of in-organic materials like ceramics, glass and metals and further organic materials such as synthetic polymers in general like resins, polycarbonate, polypropylene, polyethylene, polyethersulfone, polyester, polyoxyethylene, polyacrylonitrile, polysulfone , ethylene vinyl acetate, polyvinyl acetate, cellulose acetate, polypropylene, polytetrafluoroethylene, aramide, Polychlorotrifluoroethylene, Polyfluroethylenepropylene, polyvinylidene fluoride, polyvinylidene chloride, polystyrene, Polyamides, acetal, acrylics and further thermoplastics in general or natural polymers (also bio polymers like aliphatic polyester) in general like rubber, latex, cellulose, cellulose variations, dextran, chitin, collagen, fibrin, keratin, starch, paper, cotton, wool, flax, hemp, coconut, jute, resins, viscose rayon, human and animal organic structures or materials such as bone, tissue and further carbon and carbon element containing structures in general.

17. The bioreactor of claim 1, wherein the porous matrix is made of a material having an electrical charge applied to said porous matrix.

18. The bioreactor of claim 1, wherein the bio-reactor further comprises a temperature conditioning device.

19. The bioreactor of claim 1, wherein the feed and drainage spacers is a layer of flow-nets, screens, corrugated sheets, nettings or rib stiffeners, set of ribs or discs with a radial set of ribs or combinations thereof.

20. The bioreactor of claim 1, wherein the porous matrix is combined with, surrounded by, associated with an oxygenator, or a bubble generator or a sparging air generator arranged mutually with said bio-reactor all inside the container, the vessel or the bag.

21. The bioreactor of claim 1, wherein the bio-reactor further comprises a surrounding bag, a vessel, a container or a liquid tight enclosure.

22. The bioreactor of claim 1, wherein the matrix and/or bio-reactor are made of a material having been exposed to gamma radiation or irradiated in general for sterilization purposes.

* * * * *